US009884312B2

(12) United States Patent
Ellis et al.

(10) Patent No.: US 9,884,312 B2
(45) Date of Patent: Feb. 6, 2018

(54) DEVICE, SYSTEM, AND METHOD FOR PRODUCING ADVANCED OXIDATION PRODUCTS

(71) Applicant: RGF Environmental Group, Inc., Riviera Beach, FL (US)

(72) Inventors: Walter B. Ellis, Jupiter, FL (US); Ronald G. Fink, Jupiter, FL (US)

(73) Assignee: RGF ENVIRONMENTAL GROUP, INC., Rivera Beach, FL (US)

(*) Notice: Subject to any disclaimer, the term of this patent is extended or adjusted under 35 U.S.C. 154(b) by 167 days.

(21) Appl. No.: 14/542,450

(22) Filed: Nov. 14, 2014

(65) Prior Publication Data

US 2016/0136624 A1 May 19, 2016

(51) Int. Cl.

| | |
|---|---|
| ***A62B 7/08*** | (2006.01) |
| ***B01J 19/12*** | (2006.01) |
| ***B01J 21/12*** | (2006.01) |
| ***A61L 9/12*** | (2006.01) |
| ***A61L 9/20*** | (2006.01) |

(Continued)

(52) U.S. Cl.

CPC ................ *B01J 21/12* (2013.01); *A61L 9/04* (2013.01); *A61L 9/127* (2013.01); *A61L 9/18* (2013.01); *A61L 9/20* (2013.01); *A61L 9/205* (2013.01); *B01J 19/10* (2013.01); *B01J 21/04* (2013.01); *B01J 21/063* (2013.01); *B01J 23/10* (2013.01); *B01J 27/232* (2013.01); *B01J 35/004* (2013.01); *B01J 35/0006* (2013.01); *B01J 35/0013* (2013.01); *B01J 35/1023* (2013.01); *B01J 37/04* (2013.01); *B01J 37/08* (2013.01); *C01B 15/027* (2013.01); *A61L 2209/132* (2013.01); *A61L 2209/16* (2013.01); *A61L 2209/21* (2013.01);

(Continued)

(58) Field of Classification Search

CPC .................................. B01J 19/12; A62B 7/08

See application file for complete search history.

(56) References Cited

U.S. PATENT DOCUMENTS

| | | | |
|---|---|---|---|
| 3,744,216 | A | 7/1973 | Halloran |
| 4,684,420 | A | 8/1987 | Bryant et al. |

(Continued)

FOREIGN PATENT DOCUMENTS

| | | | |
|---|---|---|---|
| WO | 0013773 | A1 | 3/2000 |
| WO | 02102497 | A1 | 12/2002 |

OTHER PUBLICATIONS

Office Action dated Nov. 4, 2016, in U.S. Appl. No. 14/542,484, 33 pages.

(Continued)

*Primary Examiner* — Aileen B Felton

(74) *Attorney, Agent, or Firm* — Rothwell, Figg, Ernst & Manbeck, P.C.

(57) ABSTRACT

The present invention relates generally to an advanced oxidation process for providing advanced oxidation products to an environment. More particularly, the present invention provides a wick structure and hydrophilic granules for use in an advanced oxidation process, and methods of making the same. The wick structure and hydrophilic granules may be configured to collect and concentrate water vapor, so that the water vapor may subsequently be used to generate advanced oxidation products that react with and neutralize compounds in an environment, including microbes, odor causing chemicals, and other organic and inorganic chemicals.

16 Claims, 15 Drawing Sheets

(51) Int. Cl.

| | |
|---|---|
| ***A61L 9/18*** | (2006.01) |
| ***C01B 15/027*** | (2006.01) |
| ***B01J 19/10*** | (2006.01) |
| ***B01J 21/04*** | (2006.01) |
| ***B01J 21/06*** | (2006.01) |
| ***B01J 23/10*** | (2006.01) |
| ***B01J 27/232*** | (2006.01) |
| ***B01J 35/00*** | (2006.01) |
| ***B01J 35/10*** | (2006.01) |
| ***B01J 37/04*** | (2006.01) |
| ***B01J 37/08*** | (2006.01) |
| ***A61L 9/04*** | (2006.01) |

(52) U.S. Cl.
CPC *B01J 2219/0875* (2013.01); *B01J 2219/1203* (2013.01)

(56) References Cited

U.S. PATENT DOCUMENTS

| | | | |
|---|---|---|---|
| 4,892,712 | A | 1/1990 | Robertson et al. |
| 5,002,920 | A | 3/1991 | Yoshimoto et al. |
| 5,187,137 | A | 2/1993 | Terui et al. |
| 5,523,058 | A | 6/1996 | Umemura et al. |
| 5,933,702 | A | 8/1999 | Goswami |
| 5,935,525 | A | 8/1999 | Lincoln et al. |
| 6,024,929 | A | 2/2000 | Ichikawa et al. |
| 6,053,968 | A | 4/2000 | Miller |
| 6,063,343 | A | 5/2000 | Say et al. |
| 6,093,676 | A | 7/2000 | Heller et al. |
| 6,238,631 | B1 | 5/2001 | Ogata et al. |
| 6,315,963 | B1 | 11/2001 | Speer |
| 6,404,033 | B1 | 1/2002 | Chang et al. |
| 6,368,668 | B1 | 4/2002 | Kobayashi et al. |
| 6,418,960 | B1 | 7/2002 | Mintz et al. |
| 6,444,176 | B1 | 9/2002 | Yoshinaga et al. |
| 6,546,883 | B1 | 4/2003 | Fink et al. |
| 6,569,386 | B1 | 5/2003 | Ko et al. |
| 6,752,970 | B2 | 6/2004 | Schwartz et al. |
| 6,773,682 | B1 | 8/2004 | Benda |
| 6,784,440 | B2 | 8/2004 | Fink et al. |
| 6,972,415 | B2 | 12/2005 | Schaible et al. |
| 7,160,566 | B2 | 1/2007 | Fink et al. |
| 7,988,923 | B2 * | 8/2011 | Fink ........................ A61L 9/205 422/121 |
| 8,048,370 | B1 | 11/2011 | Barnes |
| 2002/0033327 | A1 | 3/2002 | Benda et al. |
| 2002/0098109 | A1 | 7/2002 | Nelson et al. |
| 2002/0155027 | A1 | 10/2002 | Gutman |
| 2003/0127753 | A1 | 7/2003 | Bachert |
| 2003/0150708 | A1 | 8/2003 | Fink |
| 2003/0230477 | A1 | 12/2003 | Fink et al. |
| 2004/0005252 | A1 | 1/2004 | Siess |
| 2004/0016887 | A1 | 1/2004 | Fink et al. |
| 2004/0056201 | A1 | 3/2004 | Fink et al. |
| 2004/0156959 | A1 | 8/2004 | Fink et al. |
| 2004/0197243 | A1 | 10/2004 | Schwartz et al. |
| 2004/0223908 | A1 | 11/2004 | Holladay et al. |
| 2005/0008549 | A1 | 1/2005 | Hsu |
| 2005/0185392 | A1 | 8/2005 | Walter et al. |
| 2005/0186124 | A1 | 8/2005 | Fink et al. |
| 2005/0186871 | A1 | 8/2005 | Hockaday |
| 2006/0144690 | A1 | 7/2006 | Fink et al. |
| 2007/0110860 | A1 | 5/2007 | Fink et al. |
| 2009/0053694 | A1 | 2/2009 | Kriksunov |
| 2012/0019917 | A1 * | 1/2012 | Riebel ................ B01D 53/8668 359/599 |
| 2012/0234166 | A1 | 9/2012 | Markham et al. |

OTHER PUBLICATIONS

Final Office Action dated Jun. 5, 2017, in U.S. Appl. No. 14/542,484, 20 pages.

* cited by examiner

DEVICE, SYSTEM, AND METHOD FOR PRODUCING ADVANCED OXIDATION PRODUCTS

CROSS REFERENCE TO RELATED APPLICATION

This application is related to U.S. patent application Ser. No. 14/542,484, filed on Nov. 14, 2014, concurrently herewith and incorporated herein by reference.

BACKGROUND OF THE INVENTION

1. Field of the Invention

The present invention relates generally to an advanced oxidation process for providing advanced oxidation products to an environment. More particularly, the present invention provides a wick structure and hydrophilic granules for use in an advanced oxidation process, and methods of making the same. The wick structure and hydrophilic granules may be configured to collect and concentrate water vapor, so that the water vapor may subsequently be used to generate advanced oxidation products that react with and neutralize compounds in an environment, including microbes, odor causing chemicals, and other organic and inorganic chemicals.

2. Description of Related Art

Germicidal ultraviolet light rays have been used for inactivating microorganisms such as viruses and bacteria. Germicidal ultraviolet light, however, is effective in reducing only the airborne microorganisms that pass directly through the light rays, and has little to no effect on gasses, vapors, or odors.

Alternatively, advanced oxidation processes may be used to eliminate microorganisms, as well as gasses, vapors, and odors. In an advanced oxidation process, advanced oxidation products ("AOPs") are produced, and subsequently destroy and/or inactivate undesired compounds in the environment. The production of AOPs may be catalyzed by ultraviolet light.

Commonly-owned U.S. Pat. No. 7,988,923, incorporated herein by reference in its entirety, describes a device, system, and method for using UV light to generate advanced oxidation products ("AOPs") in an advanced oxidation process. In this system, a light source producing multiple wavelengths of UV light is provided adjacent to a catalytic surface of a catalytic target structure. The catalytic surface is coated with a thin coating comprising hydrophilic material, thus promoting hydration of the catalytic surface from ambient moisture. Ozone and other AOPs are formed when the UV light reacts with the hydrate on the photocatalytic surfaces, and also with the air within the catalytic target structure. Additionally, ozone decomposition reactions occur, and result in the production of a variety of AOPs. The AOPs produced by this system may then be used to eliminate gasses, vapors, odors, and/or microbes in the environment.

There exists a need in the art, however, for a device, system, and method for a significantly improved oxidation process to reduce microbes and odors in an environment. Specifically, there exists a need for a device, system, and method that promote high efficiency formation AOPs. Even more specifically, there is a need for a device, system, and method configured to produce high levels of hydro peroxides for used in advanced oxidation processes.

SUMMARY OF THE INVENTION

The present invention provides a device, system, and method utilizing an advanced oxidation process to react with and neutralize compounds in an environment, including microbes, odor causing chemicals, and other organic and inorganic chemicals. The device, system, and method of the present invention employ a wick structure to collect and concentrate water vapor, so that the water vapor may subsequently be used to generate advanced oxidation products. These advanced oxidation products comprise strong and effective oxidizers that react with undesired compounds in an environment to destroy and/or inactivate the undesired compounds.

In accordance with an embodiment of the present invention, an apparatus for generating advanced oxidation products is provided. The apparatus comprises a wick structure comprising a porous base material and having an interior surface and an exterior surface. At least one high frequency ultrasonic emitter is targeted to the interior surface of the wick structure. The apparatus further comprises a light source, and a chamber wherein the formation of advanced oxidation products occurs disposed adjacent to the interior surface of the wick structure. The light source may be, for example, an ultraviolet light source or a visible light source. In the apparatus, ultrasonic energy produced by the ultrasonic emitter is targeted to the interior surface of the wick structure by one or more digital reflectors, such that sonic energy is spread across the interior surface of the wick structure.

The apparatus is intended to be used as a modular system that can either be used singularly or in plurality (limited only by the specific application). The apparatus itself may be adapted to conform to multiple types of installations. In one embodiment the apparatus is mounted via an attached plate to facilitate treatment in many different types of installations, such as in an HVAC system (e.g., in an AC duct system). In yet another embodiment the apparatus is attached to a rigid structure (sometimes with a fan assembly) to facilitate treatment of air in a multitude of applications. In alternative embodiments of the invention, the apparatus may additionally be configured to repel nuisance rodents and insects.

In one aspect of the present invention, the wick structure comprises a porous base material that comprises a hydrophilic material, a catalytic material, and a ceramic matrix. The hydrophilic material is formulated to absorb and release water. In embodiments, the hydrophilic material comprises anhydrous magnesium carbonate. The catalytic material may comprise titanium dioxide, wherein at least a portion of the titanium dioxide is in anatase crystal form. The ceramic matrix may comprise at least one of cerium oxide and aluminum oxide. In preferred embodiments, the hydrophilic material comprises magnesium carbonate, the catalytic material comprises titanium dioxide, and the ceramic matrix comprises cerium oxide and aluminum oxide. In some embodiments, the base material of the wick structure may further comprise one or more catalytic enhancer materials or dopants selected from the group consisting of rhodium, silver, copper, zinc, platinum, nickel, erbium, yttrium, fluorine, sodium, ytterbium, boron, nitrogen, phosphorus, oxygen, thulium, silicon, niobium, sulfur, chromium, cobalt, vanadium, iron, manganese, tungsten, ruthenium, gold, palladium, cadmium, and bismuth, and combinations thereof. The wick structure may be formed into a desired shape by molding or casting. For example, the wick structure may be formed as a longitudinal tube or as a conical shaped structure. According to an alternative embodiment of the invention, the inner and outer surfaces of the wick structure are designed to maximize surface area. Preferably, at least one of the inner and the outer surfaces of the wick structure comprises a ridged or pleated design, or comprises convex nodules.

Advanced oxidation products are produced according to a multi-step method. In accordance with exemplary embodiments of the present invention, an air mass comprising water vapor is flowed adjacent to an exterior surface of the wick structure. The water vapor is condensed into liquid water at the exterior surface of the wick structure. The liquid water is moved from the exterior surface of the wick structure to the interior surface of the wick structure along a differential moisture concentration gradient. The liquid water is then vaporized at an interior surface of the wick structure. In exemplary embodiments, the vaporization is caused at least partially by ultrasonic energy produced by a high frequency ultrasonic emitter. The water vapor is then converted into advanced oxidation products in a chamber adjacent to the interior surface of the wick structure.

Advantageously, this process not only treats the air in the environment with germicidal ultraviolet light energy, visible light energy, or infrared light energy, but it also has the added effect of continuing to treat the air even after it leaves the area surrounding the target surface. This process is very effective at reducing microbes, as well as reducing odors and other chemicals in the environment. This is a significant advantage over conventional ultraviolet light and advanced oxidation systems, which only reduce microbes and compounds at the point of treatment. The advanced oxidation gas created by the disclosed process, according to exemplary embodiments of the present invention, comprises safe and environmentally friendly oxidizers, including hydro peroxides, that revert back to oxygen and hydrogen as they react with contaminants. This process also requires no maintenance or technician intervention. The process is passive in operation and the surface of the wick structure acts as a catalyst to create the advanced oxidation reactions without actually affecting the target surface itself. This advanced oxidation device, system, and method is much more effective at destroying microbes than conventional germicidal ultraviolet light and PCO (photocatalytic oxidation) systems. Further, the present invention promotes increased efficiencies of the AOP reactions compared to prior art designs, i.e. with a given input of energy, more reactants and AOPs are formed. Additionally, the novel advanced oxidation device, system, and method of the present invention reduces odors in an environment, which germicidal ultraviolet light systems fail to do. The surface of the target being energized by the light along with the surrounding air creates advanced oxidation product while not producing nitric oxide gas or nitric acid, which are recognized irritants and pollutants that are harmful to humans and animals.

In accordance with other embodiments of the present invention, hydrophilic granules configured for use in an advanced oxidation process are provided. The hydrophilic granules comprise a porous base material that comprises a hydrophilic material, a catalytic material, and a ceramic matrix. The hydrophilic material is formulated to absorb and release water. In embodiments, the hydrophilic material comprises anhydrous magnesium carbonate. The catalytic material may comprise titanium dioxide, wherein at least a portion of the titanium dioxide is in anatase crystal form. The ceramic matrix may comprise at least one of cerium oxide and aluminum oxide. In preferred embodiments, the hydrophilic material comprises magnesium carbonate, the catalytic material comprises titanium dioxide, and the ceramic matrix comprises cerium oxide and aluminum oxide. In exemplary embodiments, the base material of the hydrophilic granules may further comprise a catalytic enhancer material selected from the group consisting of rhodium, silver, copper, zinc, platinum, nickel, erbium, yttrium, fluorine, sodium, ytterbium, boron, nitrogen, phosphorus, oxygen, thulium, silicon, niobium, sulfur, chromium, cobalt, vanadium, iron, manganese, tungsten, ruthenium, gold, palladium, cadmium, and bismuth, and combinations thereof. The hydrophilic granules of the present invention may be incorporated into a device used to generate advanced oxidation products. Specifically, the hydrophilic granules may be encased in a layered module, comprising a screen configured to contain the granules. The screen may have a circular or semicircular geometry, with a higher surface area at the exterior surface of the screen than at the interior surface of the screen. In some embodiments, the screen may be pleated.

A method for producing a hydrophilic base material is also provided. The method comprises providing, in a reaction chamber, a reaction mixture comprising hydrophilic material precursors, catalytic material precursors, ceramic matrix precursors, and a solvent. The hydrophilic material precursors may comprise magnesium oxide. The catalytic material precursors may comprise titanium tetraisopropoxide. The ceramic matrix precursors may comprise cerium oxide and aluminum oxide. The atmosphere in the reaction chamber is pure carbon dioxide gas at a specified temperature and pressure. The reaction mixture is mixed, while maintaining the temperature and the pressure of the reaction chamber, for a predetermined period of time to form a slurry. Optionally, at least one of aluminum (III) oxide and silicon dioxide may be added to the slurry. Additionally, one or more catalytic enhancers or dopants may also optionally be added to the slurry. The slurry is solidified to form a congealed mass, and the congealed mass is dried to form a solid material.

BRIEF DESCRIPTION OF THE DRAWINGS

The accompanying drawings, which are incorporated herein and form part of the specification, illustrate various embodiments of the present invention and, together with the description, further serve to explain the principles of the invention and to enable a person skilled in the pertinent art to make and use the invention. In the drawings, like reference numbers identify identical or functionally similar elements.

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1A:
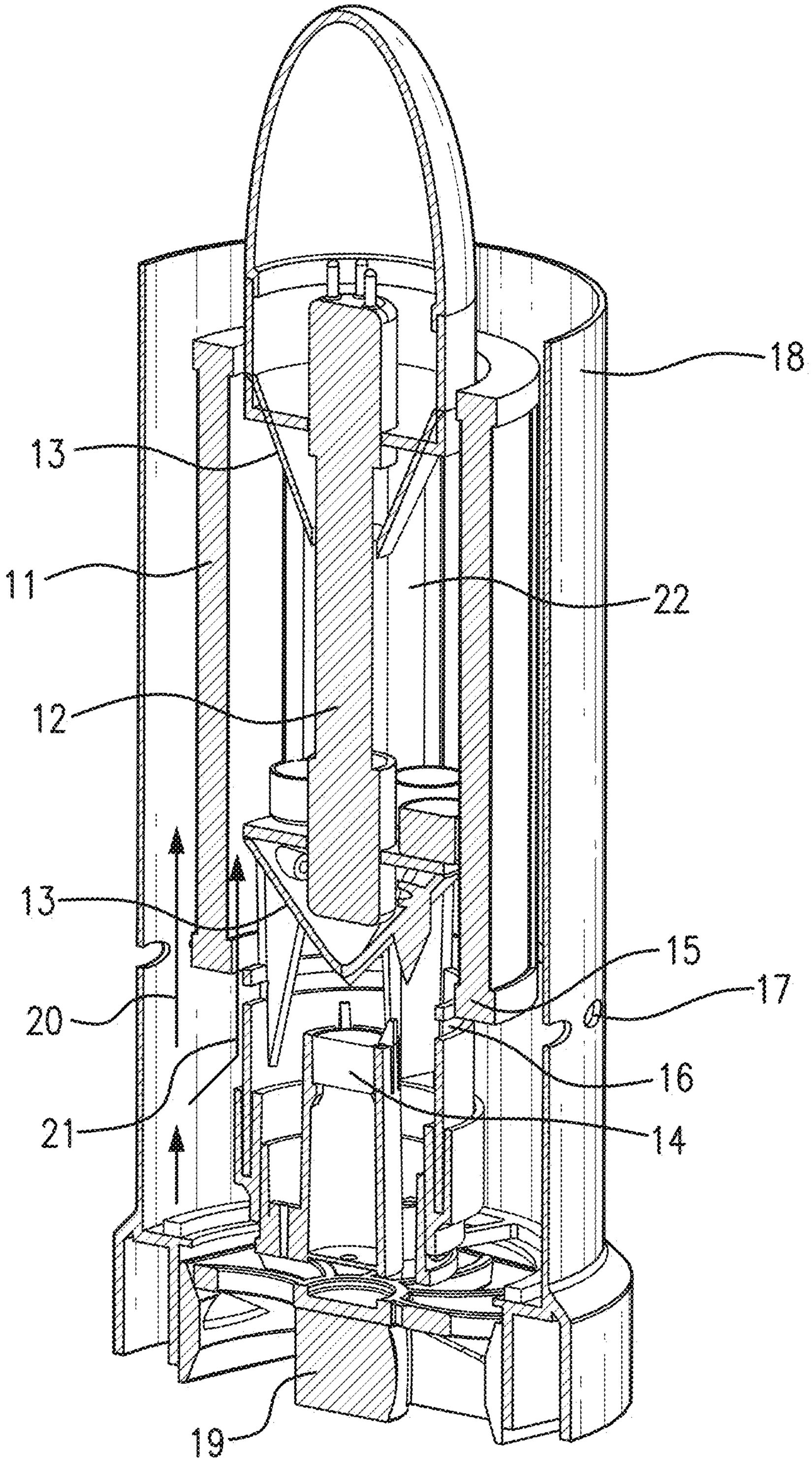
FIG. 1A illustrates an apparatus for generating advanced oxidation end products comprising a wick structure and a Reflected Electro Mechanical Energy System, in accordance with exemplary embodiments of the present invention.

Detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention.

Overview

A device, system, and method for producing advanced oxidation products utilizing advanced oxidation processes are provided. Advanced oxidation products (AOPs) are much more effective than traditional oxidants at reacting with compounds, such as microbes, odor causing chemicals, and other inorganic and organic chemicals. Advanced oxidation products are considerably stronger than typical cleaning agents such as chlorine. Generally, advanced oxidation products will react with compounds that typically will not react with other common oxidants. The device, system, and method of the present invention are specifically focused at promoting the production of the peroxide species hydrogen peroxide, but can also generate numerous other AOPs. Advanced oxidation products formed by advanced oxidation processes in accordance with various embodiments of the instant invention include, hydroxyl radicals, hydro peroxides, ozonide ions, hydroxides, and super oxide ions.

The first step for forming advanced oxidation products using the devices, systems, and methods of the present invention is targeting the capture of water vapor found within air, e.g. ambient air and/or duct air. Capture of water vapor is facilitated by the use of a novel wick structure, described below in detail. The wick structure of the present invention is comprised of hydrophilic materials coupled with an extremely high internal surface area that promotes extreme absorption of water vapor.

As water vapor from the air is absorbed onto the exterior surface of the wick structure from the ambient air, the gas phase water vapor changes into liquid form. The liquid water is then transported via molecular transport across the thickness of the wick structure, where it is ultimately released, rapidly and continually, into an advanced oxidation reaction chamber (AORC). The actual hydraulic movement across the wick structure is induced by creating a differential moisture concentration gradient within the wick structure itself. As explained in further detail below, the differential moisture concentration gradient driving hydraulic movement is generated by providing heat and ultrasonic energy at the inner surfaces of the wick structure.

Upon arriving at the inner surface of the wick structure, the liquid water then quickly transforms back to the gas phase as vaporized water. This gas-liquid-gas phase pump (GLG-Pump) mechanism is designed specifically to collect the exterior ambient humidity and then release and concentrate it inside the AORC.

AOPs may then be formed from the water vapor in the AORC by several different methods. In exemplary embodiments, multi-wavelength UV light sources (10-400 nm) are targeted onto the inner surface of the wick structure. AOPs are generated when light energy from the ultraviolet light source reacts with oxygen, ozone (if desired), water present on or in the wick structure, and one or more photocatalytic materials provided integrally in the wick structure. The inventors have surprisingly found that use of the novel wick structure described herein also allows for generation of AOPs alternatively using visible (400 nm-750 nm), or other forms of light such as near infrared light (750 nm-2500 nm). AOPs may also be produced via targeted ultrasonic sonolysis reactions within the wick structure itself, and also within the AORC. Additional sonolysis and photocatalytic reactions can take place in a secondary AOP reaction chamber, in accordance with alternative embodiments of the disclosed devices, systems, and methods These various method steps, and the components utilized therein, will be described in further detail below.

Wick Structure

The wick structure comprises a base material including a hydrophilic material, a catalytic material, and a ceramic matrix. The base material of the wick structure is full of tiny channels and connected pores equating to a huge internal surface area, in excess of 750 $m^2$ per gram. The higher the porosity of the base material, the more effective the hydraulic attraction (water absorption), and the more surface area available for photocatalytic reactions to occur.

Figure 3A:
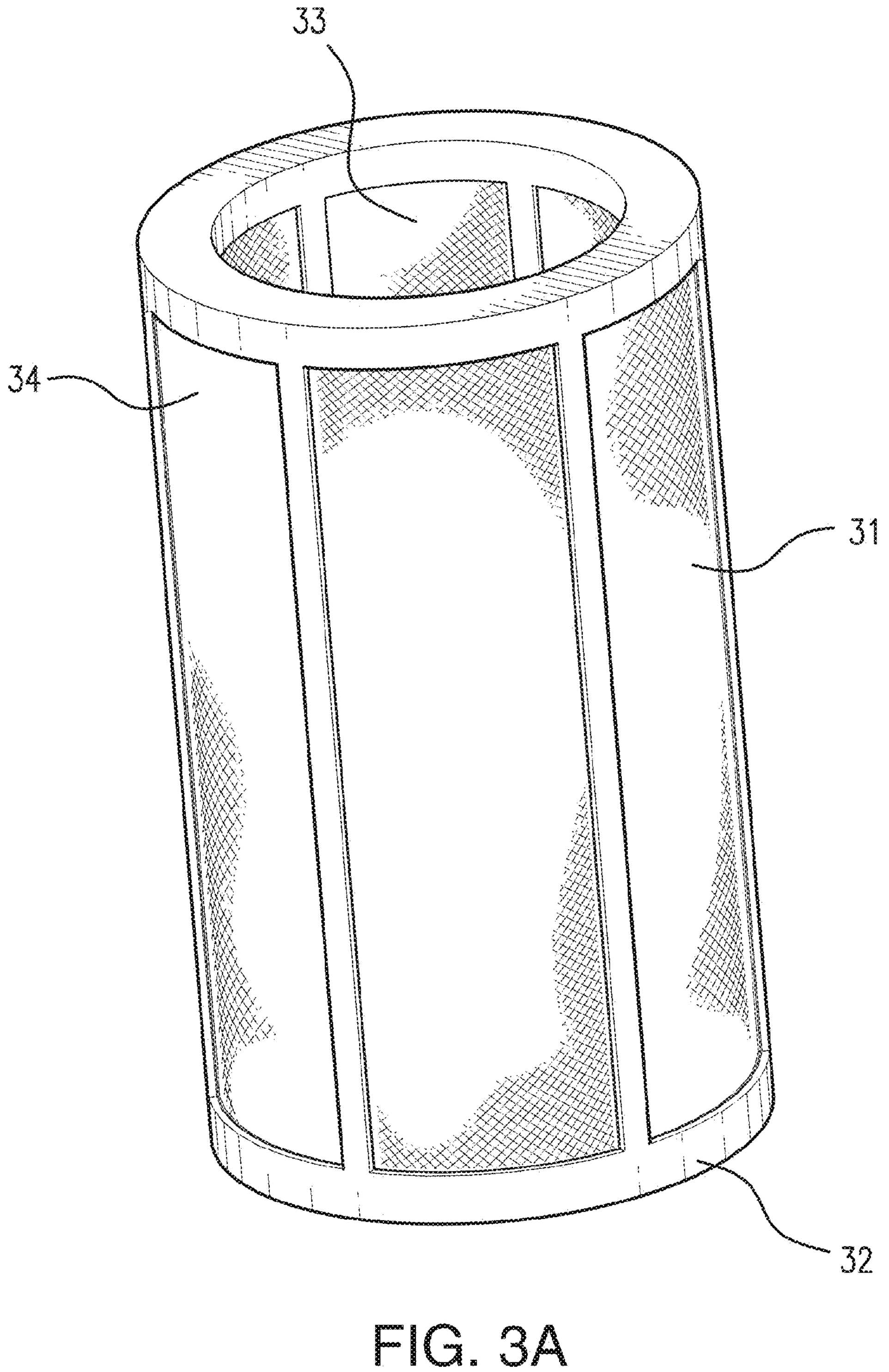
FIGS. 3A, 3B, and 3C illustrate various embodiments of the wick structure of the present invention.
Figure 3B:
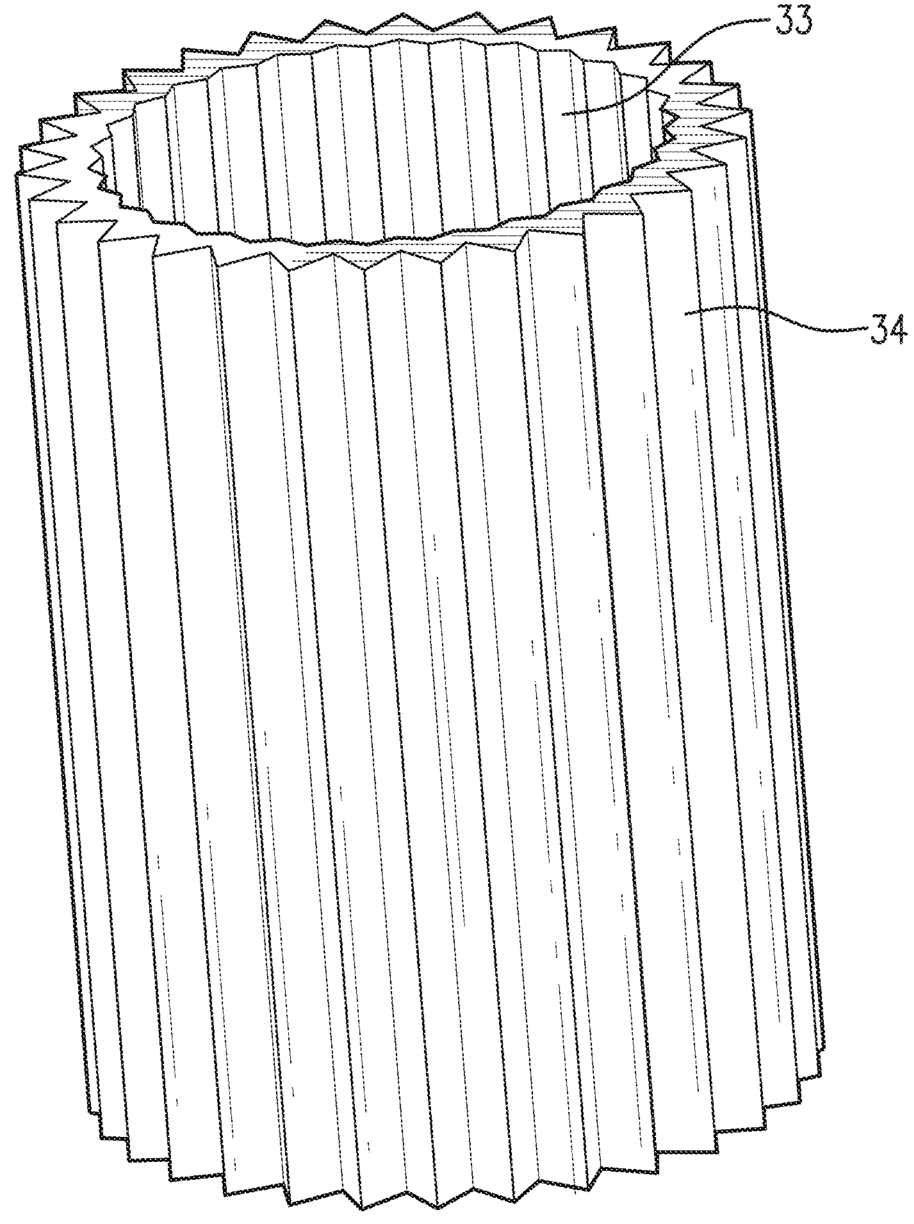
Figure 3C:
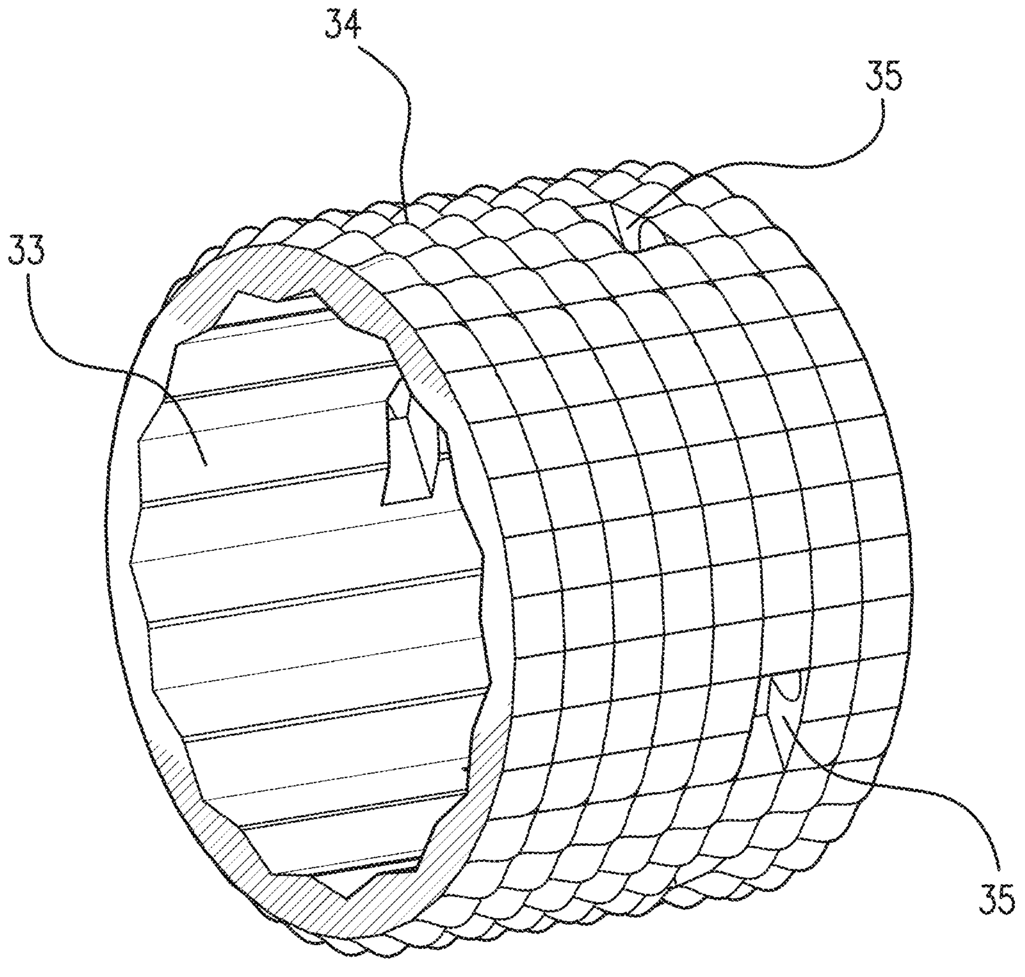

The wick structure may be provided in several different forms, as shown in FIGS. 3A, 3B, and 3C. FIG. 3A depicts a wick structure comprising a screen 31 with an outer surface 34 and an inner surface 33 configured to contain hydrophilic granules. The granules may have a diameter in the range of 0.05 mm to 2.5 mm, or a diameter that is greater than or equal to than 2.5 mm. The screen contains the granules, while also exposing the granules to ambient moisture at the exterior surface 34, and to ultrasonic energy and heat at the inner surface 33. The screen may have a circular or semicircular geometry, having a larger surface area at the exterior surface 34 of the screen than at the interior surface 33 of the screen. In some embodiments, the screen may be pleated or may comprise nodules. The screen may be disposed in a holder 32 to facilitate incorporation of the wick structure into an apparatus for generating AOPs. In exemplary embodiments, the geometry of the exterior surface of the wick structure is configured to maximize the effective surface area. FIG. 3B depicts a wick structure which has been cast into a pleated shape. In this embodiment, both the inner 33 and the outer 34 surfaces of the wick structure are pleated to maximize the surface area of each of these surfaces. In other embodiments, only one of the surfaces is pleated. The number and size of the pleats may be determined by a person of ordinary skill in the art, based on the required AOP production for the specific application. In FIG. 3C, a wick structure having an outer surface 34 comprising convex nodules is shown. The inner surface 33 of may also comprise nodules, or pleats, or be smooth. Various holes 35 are provided in the wick structure, to allow for sonic energy to pass through. The wick structures of FIGS. 3B and 3C may also be disposed in a holder (not shown) to facilitate incorporation of these wick structures into devices for generating AOPs.

In preferred embodiments, the surface area of exterior surface of the wick structure is at least 50% greater than that of the surface area of the interior surface. This ensures that the collected vapor will be concentrated when delivered to the inner surface of the wick structure.

The body of the wick structure, whether in molded or granular form, comprises a base material comprising a hydrophilic material, a catalytic material, and a ceramic matrix. The characteristics of each of these wick structure components are described below.

The hydrophilic material of the wick structure is formulated to have the unique ability to absorb high quantities of water vapor (i.e. to be extremely hydrophilic). Notably, the hydrophilic material is formulated to also re-release the vast majority of this absorbed water back into the air. It is preferred that the hydrophilic material in the wick structure comprises anhydrous magnesium carbonate. Additionally, it is preferred that the magnesium carbonate is amorphous. In testing performed by the inventors, it was found that the magnesium carbonate can be formulated to re-release up to 95% of the absorbed water, in exemplary embodiments of the instant invention.

The catalytic material in the wick structure plays a key role in catalyzing the formation of advanced oxidation products within and at the surface of the wick structure. The catalytic material is preferably titanium dioxide. At least a portion of the titanium dioxide in the wick structure is in anatase crystal form. In exemplary embodiments, almost all of the titanium dioxide is in anatase crystal form, i.e. at least 90%, at least 95%, or at least 99% of the titanium dioxide is in anatase crystal form. In exemplary embodiments, at least a portion of the titanium dioxide is in the form of nanoparticles.

The ceramic matrix provides structural support, and allows for production of a more rigid final material. Preferably, the ceramic matrix comprises cerium oxide and aluminum oxide ($Al_2O_3$). The cerium oxide acts as a binder with the $Al_2O_3$. Additionally, the cerium oxide has inherent hydration properties, i.e. it is hydrophilic, and thus further enhances the effect of the $MgCO_3$ described above. The cerium oxide also has inherent catalytic properties.

In addition, one or more known catalytic enhancers or dopants can optionally be added during the process of forming the wick structure, such that the catalytic enhancer(s) or dopant(s) are integrated into the final wick structure. Known catalytic enhancers and dopants appropriate for inclusion in the wick structure include, but are not limited to, rhodium, silver, copper, zinc, platinum, nickel, erbium, yttrium, fluorine, sodium, ytterbium, boron, nitrogen, phosphorus, oxygen, thulium, silicon, niobium, sulfur, chromium, cobalt, vanadium, iron, manganese, tungsten, ruthenium, gold, palladium, cadmium, and bismuth, and combinations thereof.

A unique feature of the wick structure base material is its ability to be cast into unique shapes and forms. This allows for precision control of its final shape and, by design, also its structural strength. The structure's shape and design can be altered based on the average humidity of the ambient environment of its intended use. For example, by increasing the ratio of the outer surface area to inner surface area, a targeted increase in available AORC water vapor will occur internal to the wick structure. For example, in a ambient environment with an average relative humidity of 35%, increasing the outer to inner surface ratio to 3:1 can achieve a 99.9% relative humidity microclimate at the inner surface.

Scanning electron micrographs of a base material for a wick structure are shown in FIG. 4A (50× magnification) and FIG. 4B (1000× magnification). As shown in the images, the wick structure's base material has a sponge-like structure of magnesium carbonate, with crystals of anatase titanium dioxide infused throughout, and interlaced with a cerium oxide and aluminum oxide ceramic matrix. In the referenced micrographs, the darker nodules represent anatase $TiO_2$ crystals.

As further illustrated in the micrographs, the surface of the wick structure base material is generally irregular and uneven, creating microprojections extending from the surface. The presence of such microprojections further increases the effective surface area. In FIG. 4A, a large pore 41 can be seen at the upper left hand corner of the micrograph.

Reflected Electro Mechanical Energy System

Figure 1B:
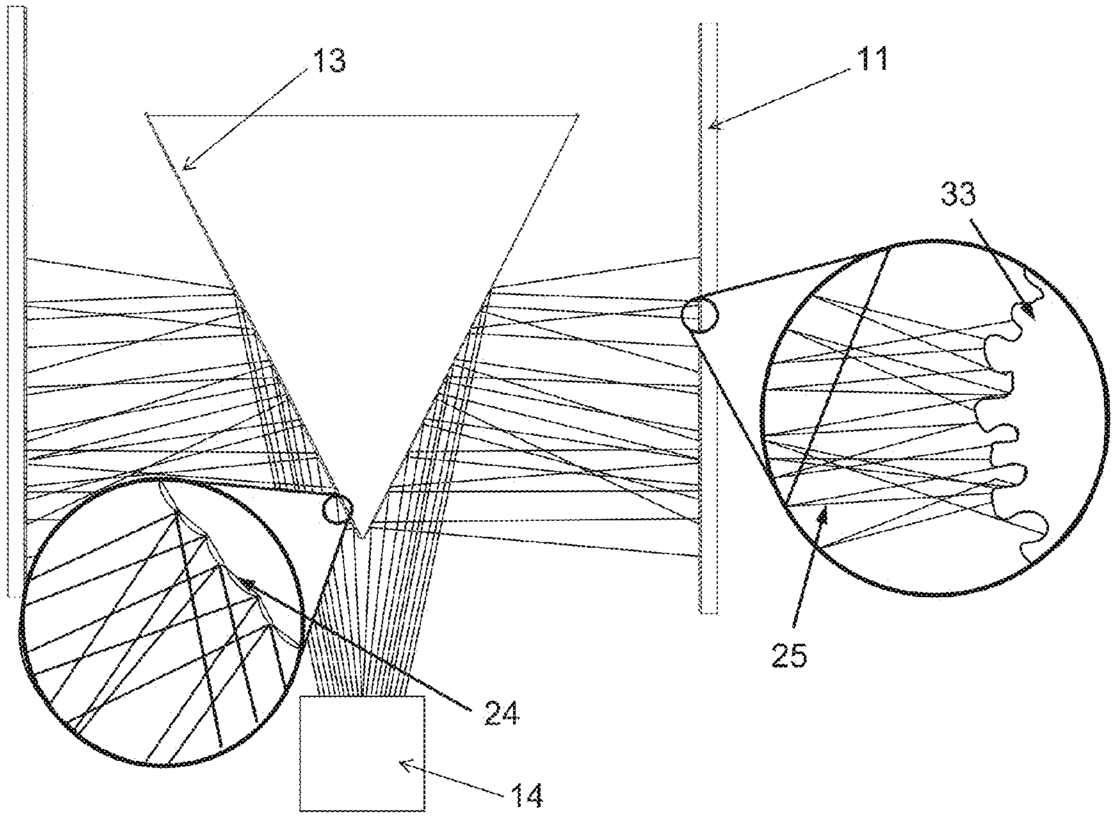
FIG. 1B shows various components of the Reflected Electro Mechanical Energy System in greater detail.

In exemplary embodiments of the invention, a Reflected Electro Mechanical Energy System is used to facilitate movement of liquid water across the thickness of the wick structure, and also to produce AOPs via sonolysis reactions. As shown in FIGS. 1A and 1B, the system comprises one or more high frequency ultrasonic emitters 14 and one or more digital reflectors 13 which, together, are configured to induce sonic energy 25 into the absorbed water present within the wick structure 11.

The one or more ultrasonic energy emitters provide ultrasonic energy in two simultaneous waves. The first wave has a frequency in the range of 20-30 kHz, and the second wave has a frequency in the range of 1.5-4 MhZ. Preferably, the frequency of the first wave is 26 kHz and the frequency of the second wave is 2 Mhz. The number and power of the ultrasonic emitters is determined by the size of final required structure. Those of ordinary skill in the art will recognize the size of the final structure can be configured depending on the reaction output desired and the space to output ratio required for the AOP process.

For added effect, a frequency hopping scheme can also be employed. A single ultrasonic driver is provided, wherein the driver varies the sonic transducer's emitted frequencies. The frequencies can be varied electronically, using various off-the-shelf IC chips in a custom circuit for the application. Alternatively, the frequencies can be varied mechanically by using multiple single frequency sonic transducers in an array, each one with a different frequency to get a similar net effect. Frequency hopping enhances evaporation rates by inducing resonant responses from the different mediums within the wick structure.

The digital reflectors 13 are configured to direct and evenly disperse the produced ultrasonic energy 25 onto the interior walls of the wick structure 11, as illustrated in FIG. 1B. The digital reflectors are typically made of materials such as polycarbonate, aluminum, or stainless steel. However, those of ordinary skill in the art will appreciate that many different materials may be used to achieve the desired reflection of ultrasonic energy. The shape of reflector chosen will depend on the required geometry for optimal energy distribution in each particular embodiment of the invention. For example, the base geometry of the reflectors can be planar or conical in structure.

The digital reflectors 13 may comprise a plurality of smaller planar convex reflectors 24 that are specifically angled to reflect and disperse the ultrasonic energy onto targeted points or surfaces of the interior surface of the wick structure 33. There may be several thousand individual planar convex reflectors at the surface of each digital reflector. Typically, reflector panels are 0.0009 square inches or less, with center angles of 85 degrees.

The ultrasonic energy emitter(s) 14 and the digital reflector(s) 13 are configured such that transmitted sonic waves 25 make contact with a reflector 13, and the sonic waves 25 are subsequently deflected toward specific targeted surfaces of the wick structure 11, while also being dispersed in a conical pattern. Each reflected wave will angle outward and then overlap the path of its adjacent reflector plane, effectively spreading the sonic energy 25 across the entire inner wall 33 of the wick structure 11 at multiple path angles. By deflecting the sonic energy into multiple sonic pathways and angles of contact, the digital reflector 13 design essentially bathes the entire irregular micro surfaces of the wick structure inner surface 33 with sonic energy. This reflector design essentially simulates the presence of thousands of individual ultrasonic emitting sources, all directed to specific locations across the entire wick structure inner surface. Using this multipath digital reflector design in lieu of a single flat unidirectional reflector completely eliminates any line of sight shadowing of the rough wick structure surfaces. In other words, the reflector design disclosed herein provides for much more complete surface coverage, and with a much lower output power requirement, to achieve the same coverage achieved by other configurations having additional components and complexity.

The high frequency sonic waves striking the hydrophilic surfaces of the wick structure initiate micro oscillations of the water molecules within the airspaces of the wick structure. This process is most effective when pore and inter granule spacing is greater than of 0.04 microns, with 0.10 to 10 microns being considered ideal. The induced oscillation energy forms micro partial vacuum points within the wick structure itself, which in turn lowers the partial pressure at these locations. This causes water molecules from the wick's higher pressure outer surface to move towards the lower pressure zones near the wick's interior surface.

The ultrasonic energy will also cause water droplets to begin to spontaneously cavitate at the interior surface of the wick structure. This cavitation process occurs in the water at the interior surface of the wick structure, and also in the water trapped within the smaller pores and spaces of the individual wick structure granules contained within the interior side of the wall of the wick structure. The ideal pore size to effect cavitation is from 0.003 to 0.39 microns.

In the cavitation process, micro air bubbles form and rapidly expand within the water droplets. Once each air bubble is unable to expand any further, it rapidly collapses, releasing a large amount of energy as heat. These intense micro point sources of heat (as high as 4000K) cause a localized increase in temperatures of the wick structure, specifically within the region of the wick structure adjacent to the internal surface. Notably, a very high pressure wave is released upon bubble implosion. The increased temperature in turn lowers the water vapor pressure of the internal chamber side air in close proximity to these heated wick structure surfaces, promoting vaporization of the water from the inner surfaces of the wick into the air. In addition, this same cavitation process (the rapidly collapsing air bubbles) directly causes ultrasonic atomization of the water droplets into the air. This occurs when micro droplets of water are violently expelled into the surrounding air spaces upon implosion (cavitation), leading to their instantaneous evaporation into the surrounding air. The vaporization of water at the inner surfaces of the wick structure creates a moisture gradient across the thickness of the wick structure.

Each of the processes mediated by the Reflective Electro Mechanical Energy System, including the moisture gradient, the heating of the inner surfaces due to cavitation, the vapor pressure reduction, the sonic cavitation, and the sonolysis, combine to "pull" water molecules from the wick structure's outer surface to the internal wick structure walls, and subsequently into the interior surfaces of the wick structure. This makes the water molecules available for forming AOPs.

AOPs are formed in this system in several ways. When the cavitation process occurs, as described above, a large amount of energy is released. This released energy interacts directly with the effected water droplet (i.e. the water droplet undergoing cavitation) and the individual water molecules disposed within the walls of the wick structure, adjacent to the energy release. This causes instantaneous dissociation of the water and, ultimately, recombination into various AOPs, including hydroxyl radicals, super oxides, peroxides, and hydroxides. The produced AOPs are highly reactive, and will react with and destroy other undesirable organic and inorganic chemicals found in the environment. This results in a cleaning and purifying treatment of the surrounding air of an environment. These advanced oxidation product are very short lived and highly reactive such that after reacting with the compounds in an environment the advanced oxidation products will (over a short period of time) revert to safe and harmless oxygen and water molecules.

Because of the unique ability of the wick structure to absorb high amounts of water, large quantities of water are present in the wick structure, and water is the primary compound available for reaction at the inner surfaces of the wick structure, where the sonolysis reactions occur. The water vapor adjacent to the inner surfaces of the wick structure reacts with the AOP products to produce a more stable molecule—hydrogen peroxide ($H_2O_2$). For example, the reaction of two hydroxyl radicals creates $H_2O_2$. Additionally, the reaction of one superoxide ion ($O^{2-}$) with two water molecules produces two molecules of $H_2O_2$. This results in the production of high amounts of hydrogen peroxide in the AORC. Hydrogen peroxide is a strong oxidizer that can kill microbes, such as bacteria, mold, viruses, and can also react with chemicals in the environment to reduce odors. After hydrogen peroxide has been produced in the AORC, it travels out into airspaces external to the duct or unit, and will continue to treat air within these spaces, and surfaces within these spaces. This is a distinct advantage of the devices of the instant invention over conventional UV and PCO reactors. The vapor pressure reducing activities on the interior side of the wick structure also enhance the transfer of the air mass through the device. The micro projections of the wick structure protruding into the flowing air cause an increase in the surface air turbulence. This action also increases and aids in the effective airflow and mixing at the surface boundaries. The process reduces the surface boundary layers, allowing more air to actively flow into and pass out of the surfaces and structural projections. This micro mixing effect coupled with the high mass transfer of the air flow further increases the evaporation rate, thereby increasing the transfer of the liquid water from the wick structure into a water vapor within the inner AOP chamber environment. Each of these processes combine to "pull" additional water molecules from the wick structure's outer surface to the internal wick structure walls, and subsequently into the AOP chamber interior.

Heat Source

The actual hydraulic movement and concentration across the wick structure is induced by creating a differential moisture concentration gradient within the wick structure itself. As explained above, a differential moisture concentration gradient may be formed within the wick structure by supplying targeted high frequency ultrasonic energy to mechanically oscillate the trapped water molecules bound within the internal surfaces of the wick structure. Additionally, a moisture gradient may be generated by specifically heating the inner surface of the wick structure. Heating only the surfaces of the inner wall of the wick structure results in lowering the surface vapor pressure of the interior surface of the wick structure, promoting hydraulic movement across the wall thicknesses. Heating is controlled to ensure that only the inner surface of the wick structure, including the internal channels just below the inner surface, are thermally effected. A microclimate effect at the inner surface of the wick structure is the desired outcome. It is not desired to uniformly warm the entire wall thickness of the wick structure, because a temperature gradient must be maintained in order for this secondary moisture pump process to be effective.

The heat required to heat the inner surface of the wick structure may be produced by specific thermal devices positioned adjacent to the wick structure. The thermal devices may be heaters, such as high resistance wire. Alternatively, the heat may be recovered from system components. Notably, the provision of targeted high frequency ultrasonic energy to the inner surface of the wick structure will also heat this surface. As explained above, the lower pressure at the inner wick surface caused by the provision of ultrasonic energy causes water droplets in this region to spontaneously cavitate. When this cavitation occurs, micro air bubbles form and rapidly expand within the water droplets. Once the air bubble is unable to expand any further, it rapidly collapses releasing a large amount of energy as heat. These intense micro point sources of heat (as high as 4000K) cause a localized increase in temperatures of the inner surfaces of the wick structure. In other embodiments, heat energy radiated from the light sources as infrared energy can also be harnessed to heat the inner wall surfaces of the wick structure, working in tandem with the sonolysis heating.

Activation Light Source

In addition to the advanced oxidation reactions induced by the ultrasonic sonolysis, additional AOP reactions will also take place in the system using the in situ photocatalytic surfaces of the wick structure. These additional advanced oxidation reactions occur as a direct result of applied light energy reacting with the photocatalytic surfaces. Additional reactions will also occur within the air plasma itself as the light energy reacts with the water and water-derived components (H and O) in the air.

Light energy is applied to the interior surfaces of the wick structure. The photocatalysts that are integrated directly into the wick structure react with the applied light energy. A broad wavelength of light, generally from 100-2500 nm (ultraviolet, visible, near infrared), can be used to initiate these reactions, with best results occurring when light is provided at least one of the following wavelengths: 254 nm, 280 nm, 350 nm, 365 nm, 420 nm, 450 nm, or combinations thereof, or when light is provided in the visible or infrared range Those of skill in the art will recognize that varying the amounts of the co-catalysts in the final design will change the photocatalyst activation band gap and associated capabilities (i.e. increasing the effective light wavelength for its band gap activation). Those of skill in the art will also understand that, if desired, a combination of 185 nm light and 254 nm light may be provided to optionally provide an additional AOP pathway by way of the ozone decomposition reaction, further increasing the AOP potential.

The activation light source can be any suitable light producing device, including but not limited to: low pressure mercury vapor sources, medium pressure mercury vapor sources, low pressure amalgam sources, LEDs, excimer sources, pulsed mercury/xenon arc, metal halide arc, lasers, etc. In one embodiment a low pressure mercury vapor source is preferred, as the heat generated by this type of lamp is adequate to result in the desired microclimate effect via warming the inner wall surfaces of the wick structure during its illumination.

In some embodiments, an ultraviolet light source may be used as the activation light source. In other embodiments, a visible light source may be used as the activation light source. The band gap energy required for AOP surface activation of the catalytic materials within the wick structure can be adjusted by providing different dopants in the wick structure base material.

Preferably, a broad spectrum ultraviolet light source is used to strike the surface of the interior surfaces of the wick structure, as well as to energize the surrounding atmosphere of an environment. The ultraviolet energy strikes the inner surfaces of the wick structure and activates production of hydroxyl radicals, super oxide ions and hydro peroxide on the surface. Because of the unique formulation of the wick structure, large quantities of water are collected from the air surrounding the outer surfaces of the wick structure and released into the AORC. The ultraviolet light energy energizes the catalytic molecules at the inner surface of the wick structure, causing the surface to react with water molecules primarily on the surface of the wick structure and also in the surrounding air, and causing them to split into AOPs such as hydroxyl radicals, super oxide ions, hydro peroxides, etc. in an advanced oxidation process. In this process, not only is the target surface active, but also is the air space between the inner surface of the wick structure and the ultraviolet light energy source.

Electrodes

In another embodiment, actively generated ions are introduced within the sonic field, i.e. the inner volume of the AORC wherein sonic energy is present. Introduction of these ions within the vaporization and sonolysis zone further enhances the production of the desired AOP products. These additional ions released directly within the flowing plasma of the wick structure and AORC increases the availability of the overall ionized molecular species. The hydro reactive molecules formed from the vaporization, catalytic, and sonolysis reactions are further destabilized by the high availability of this additional ionization energy. The addition of this ionization energy acts as a promoter to further drive or push the AOP reactions to produce more hydro peroxides, including hydrogen peroxide, within the AORC.

To produce the ions, actively charged ion emitters, e.g. electrodes, are positioned near or on the digital reflector surfaces. It is desirable that these ion emitters are resistant to corrosion in the harsh AOP environment. The ion emitters can be either multipoint carbon fiber, or non-oxidizing metal such as high grade stainless steel, Inconel, or even titanium). The ion emitters may also be gold plated electrodes. The ion emitters are supplied with a voltage in the range of 1.5 K to 5 K volts, with a current not exceeding 1000 micro amps.

Both positive and negatively charged ions are released, either from single or multiple locations within the sonic field.

Secondary Advanced Oxidation Reaction Chamber

In exemplary embodiments, a secondary and separate AORC can be positioned directly downstream from the wick structure, ultra sonic transducer(s), reflector assemblies, and other system components. The pretreated high humidity and ionically charged air flows from the wick structure assembly and into the secondary advanced oxidation reaction chamber. Here the very high humidity air goes through additional advanced oxidation processes.

The secondary AORC consists of additional high surface area photocatalytic targets to further react with the high humidity air. This structure can consist of folded pleats with air passages, arrayed fins, or other suitable surfaces to provide maximum light conversion into AOP reactants. The key advantage to this secondary chamber addition is that the overall dimensions can be changed to accommodate higher amounts of AOP reactants (e.g. water). The design can include multiple light sources, larger cross sections of reactive surfaces, and a longer reaction chamber length. It can be more easily constructed to accommodate longer required reaction retention times, enabling a higher contaminant concentration treatment.

Exemplary Embodiments

The various components described above may be incorporated into a device for producing AOPs. Various embodiments of such devices are described herein. The devices are intended to be used as modular systems that can either be used singularly or in plurality (limited only by the specific application). The devices may be adapted to conform to multiple types of installations.

In one embodiment of the invention, a device is provided for performing advanced oxidation reactions within an advanced oxidation reaction chamber using a Reflected Electro Mechanical Energy System. Although the device may be configured to produce a variety of AOP species, the design of this system is specifically configured to promote the production of the peroxide species hydrogen peroxide. This effect is achieved by actively collecting and concentrating water via a wick structure for the purpose of its conversion into hydrogen peroxide molecules. In this device, the wick structure is formed containing catalytic materials integral to its structure. Placement points for advanced oxidation photo catalytic surfaces are formed in situ, and in co-existence within the designed hydrating system. This unique placement of catalysts inside the hydrating structure and it associated crevices and pores further aids in the promotion of the advanced oxidation process's (AOP's). The in situ AOP reaction cycles formed are driven towards the increased production of hydrogen peroxide as they now occur within the same locations as the hydrating source, providing abundant water vapor to react with and subsequently form the hydro peroxide species. This entire device and process is accomplished using a multi-step system and approach.

In one embodiment of the invention, shown in FIG. 1, an apparatus for producing AOPs comprises a wick structure in tube form 11 substantially surrounding a light source 12, which may be for example, an ultraviolet or visible light source. The apparatus further comprises a Reflective Electro Mechanical Energy System comprising ultra-sonic transducers 14, 15, and digital ultrasonic reflectors 13. The digital reflectors 13 are configured to deflect the ultrasonic energy produced by the ultrasonic transducers toward the inner surfaces of the wick structure tube, while also dispersing the ultrasonic energy into thousands of individual conical patterns at multiple beam angles. The device may be configured with internal 16 and external 17 ultrasonic energy exit slots in order to allow a portion of the reflected sonic energy to travel from the digital reflectors into the air space external to the apparatus. Releasing ultrasonic energy into these ambient duct spaces is shown to induce uncomfortable environmental conditions to household pests, as explained further below. The apparatus may comprise a fan assembly 19 to direct air flow towards the wick structure. Each of the components described above is contained within a housing 18.

Figure 5:
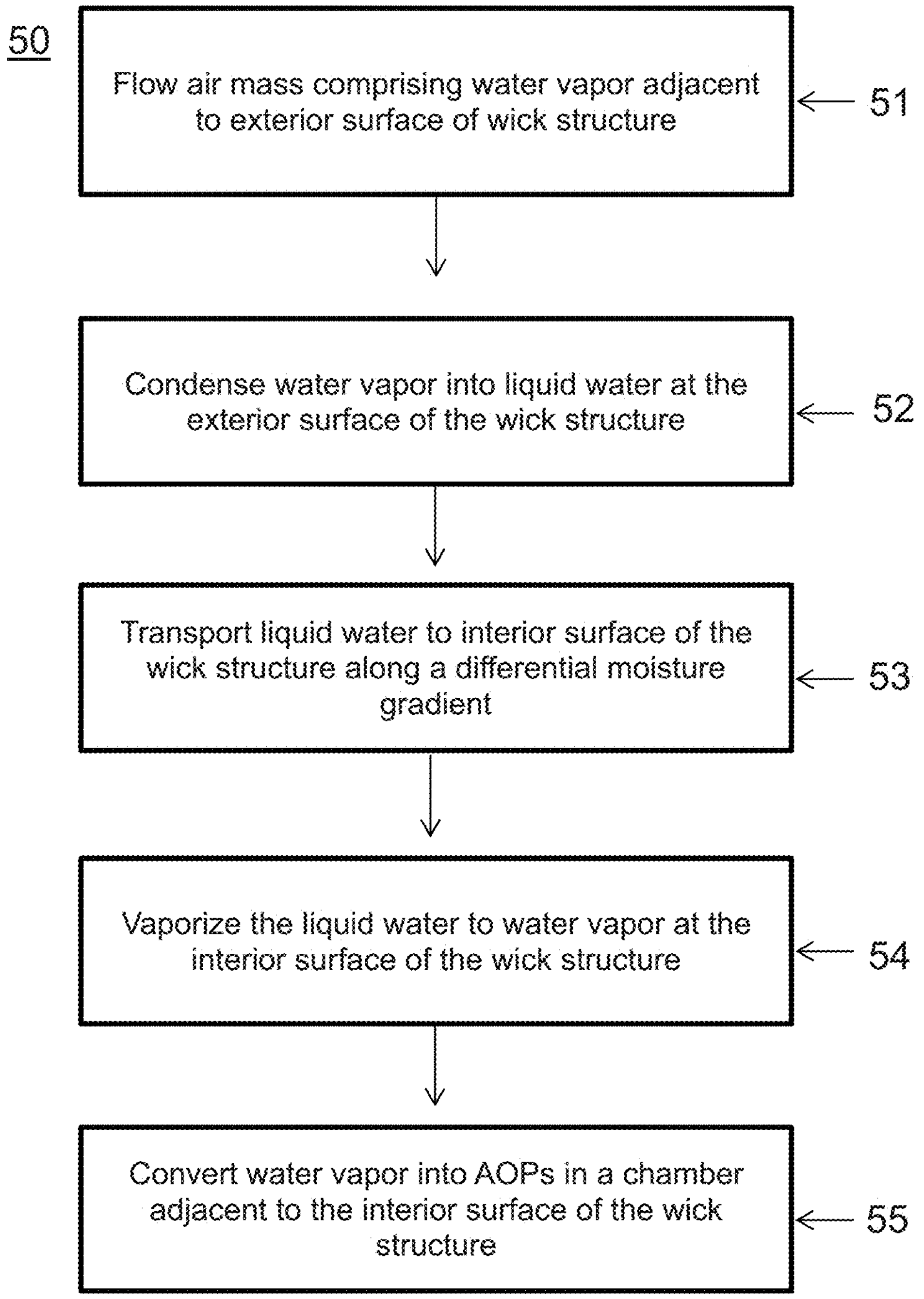
FIG. 5 is a flowchart illustrating a method for producing advanced oxidation end products in accordance with exemplary embodiments of the present invention.

Referring now to FIG. 5, a flow chart 50 illustrating a method for producing advanced oxidation products is shown. In step 51, a first air mass comprising water vapor is flowed adjacent to the exterior surface of the wick structure 11, in a space between the outer surface of the wick structure and the inner wall of the housing 18. In step 52, when this first air mass flows along the air path 20, water vapor is delivered to the exterior surface of the wick structure, which is subsequently absorbed and condensed into liquid water at the exterior surface of the wick structure. In step 53, the liquid water is subsequently transported, concentrated and vaporized to the interior surface of the wick structure along a differential moisture gradient. In step 54, the liquid water is then vaporized for use during AOP formation In step 55, AOPs are produced in the AORC 22, contained in the space between the inner surfaces of the wick structure 11 and the light source 12.

A second air mass, which is typically lower flow than the first air mass, is also simultaneously flowed along the interior surface of the wick structure 11. Air moving along this inner air path 21 mixes with the AOPs produced, and helps to distribute them. Specifically, air flowing inside the AORC pulls and mixes the AOPs and water vapor released from the inner pores and surfaces of the wick structure into the second air mass.

The second air mass is combined with the first air mass after passing through the AORC. The faster flowing first air mass (external to the wick structure) creates a low pressure zone, in essence a low or partial vacuum zone, as it passes the exit point of the second air mass (internal to the AORC). The creation of this low pressure zone actively pulls the second air mass stream into the first air mass stream, resulting in thorough and efficient mixing over a very short distance. After the first and second air masses have been combined, the combined air containing AOPs is released externally from the apparatus, and exists into ambient air (either duct or other space), so that the AOPs contained within the air mass can be further reacted and/or conveyed external to the AORC chamber for air and surface treatments.

Figure 4:
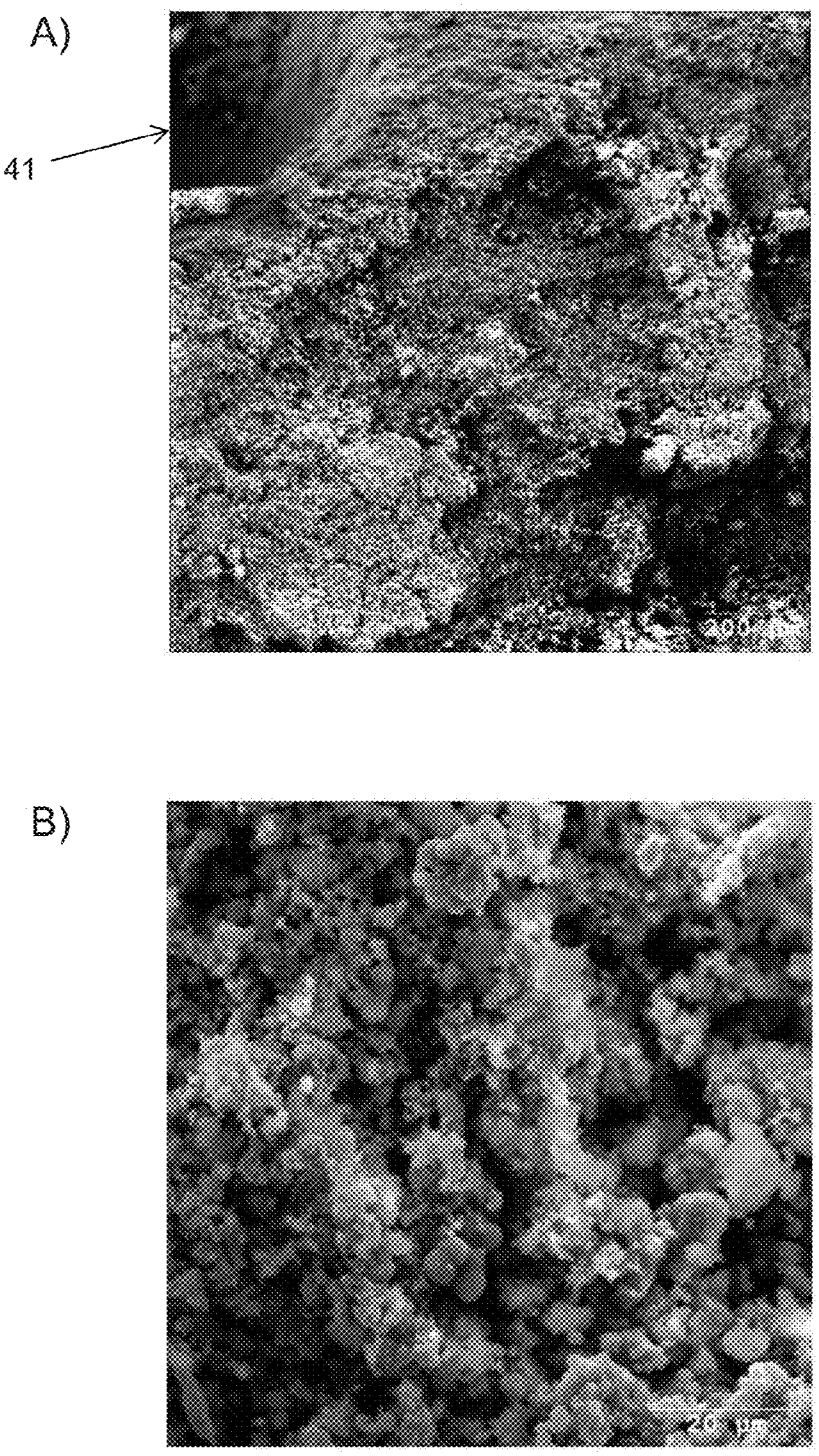
FIG. 4 provides scanning electron micrographs of the surface of a wick structure base material, in accordance with exemplary embodiments of the present invention.

Notably, the unique features of the surface of the wick structure base material also enhance movement of air through the device. As shown in FIG. 4, the surface of the wick structure has microprojections which extend into the boundary layer of air contacting the solid surfaces of the wick structure. The micro projections protruding into the flowing air cause an increase in the surface air turbulence, which reduces surface drag. This increases and aids in the effective airflow and mixing at the surface boundaries, allowing more air to actively flow into and pass out of the surfaces and structural projections. This micro mixing effect coupled with the high mass transfer of the air flow further increases the evaporation rate, thereby increasing the conversion of the liquid water from the wick structure into water vapor within the inner AOP chamber environment.

Figure 7A:
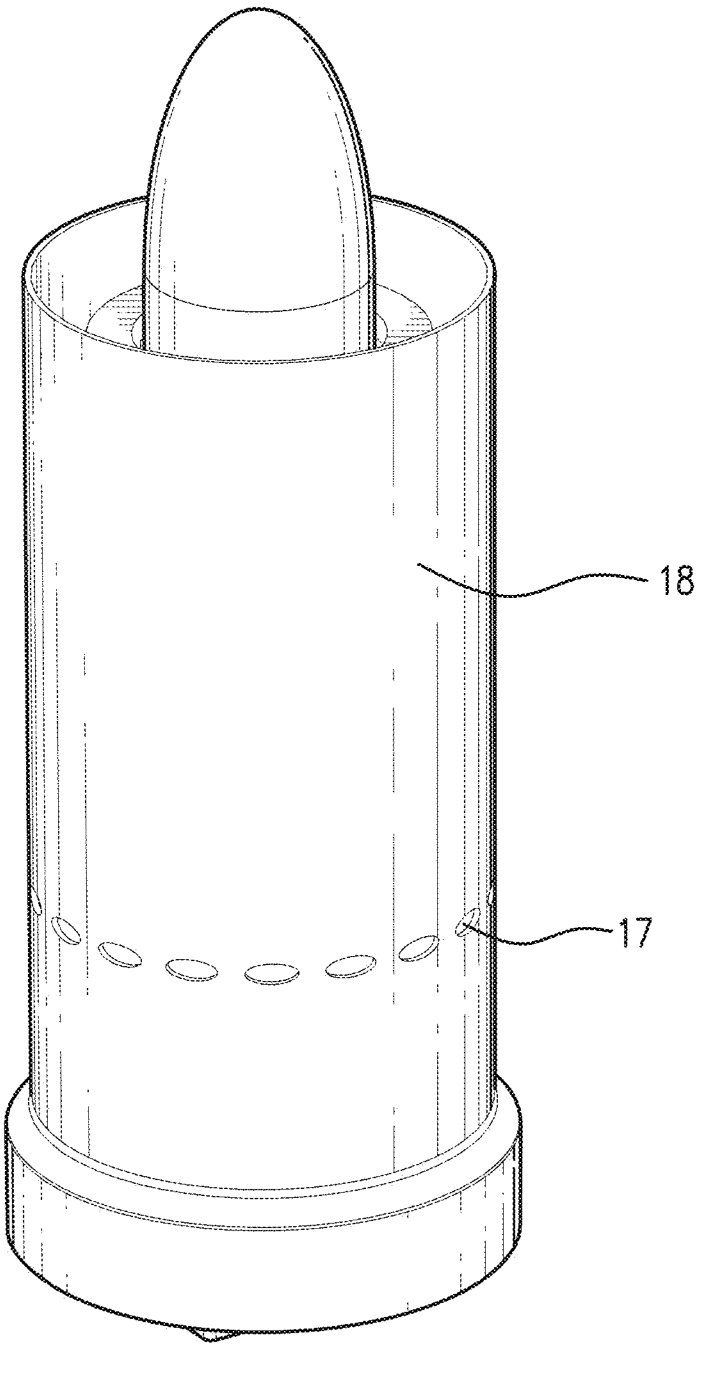
FIGS. 7A, 7B, and 7C illustrate alternative embodiments of an apparatus for generating advanced oxidation products, in accordance with exemplary embodiments of the present invention.

The device of FIG. 1A may be configured to operate as a stand-alone device, as shown in FIG. 7A. When configured as a stand-alone device, a fan may be provided to direct air into the device. This stand-alone embodiment of the device may be used for example, as an air purification system for a room.

Figure 2:
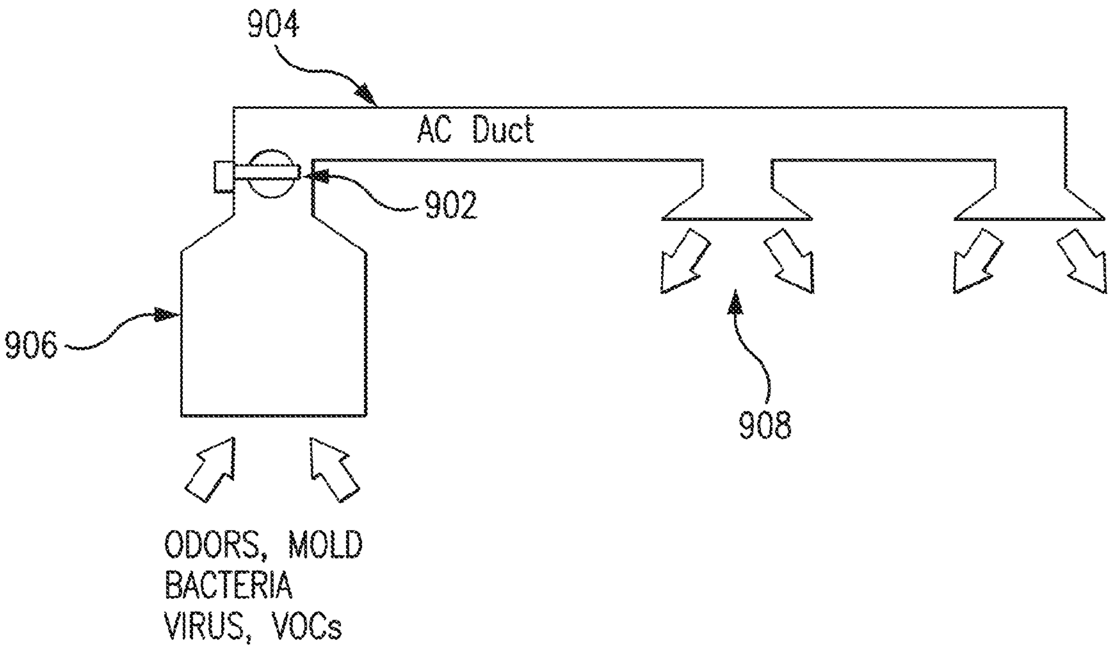
FIG. 2 illustrates a system for generating advanced oxidation end products from a device mounted in an air duct, in accordance with exemplary embodiments of the present invention.

In other embodiments, the apparatus may alternatively be mounted via an attached plate to facilitate treatment of air in many different types of installations, such as in an HVAC system (e.g., in an AC duct system). One such embodiment is shown in FIG. 2. In FIG. 2, an AOP-producing device 902 in accordance with various embodiments of the present invention is arranged and mounted onto an AC duct 904 in a mounting arrangement such that the air flow through the AC duct 904 passes and contacts the apparatus 902. The apparatus 902 extends substantially within the AC duct 904 through an opening in one of the walls of the AC duct 904 and is supported in place by a mounting plate or similar device.

An air intake 906 receives air from the building environment, which includes pollutants, odors, mold, bacteria, virus, and other undesired chemicals. As this air passes through the duct 904 it is exposed to the apparatus 902, the light source, and the advanced oxidation processes, which will substantially clean and purify the air. This air, in combination with a portion of the advanced oxidation products created in the apparatus 902, is then driven through the remaining AC duct 904. The portion of the AOPs moving with the air continue to reduce the residual pollutants as they travel down the duct 904 with the air. Any remaining advanced oxidation products then exit 908 into the room, where they continue to quickly reduce any additional ambient pollutants encountered. Additionally, if a UV light source is used, germicidal UV light rays help destroy microorganisms, such as germs, molds, viruses, and bacteria passing through the AC duct 904. In this way, the advanced oxidation process apparatus 902 in this application, thereby cleans and purifies air for use in a building environment. Additionally, this apparatus will also kill microbes on surfaces external to the device, such as door knobs, duct surfaces, or other stainless steel surfaces. This feature is a key advantage over prior art devices.

Figure 7B:
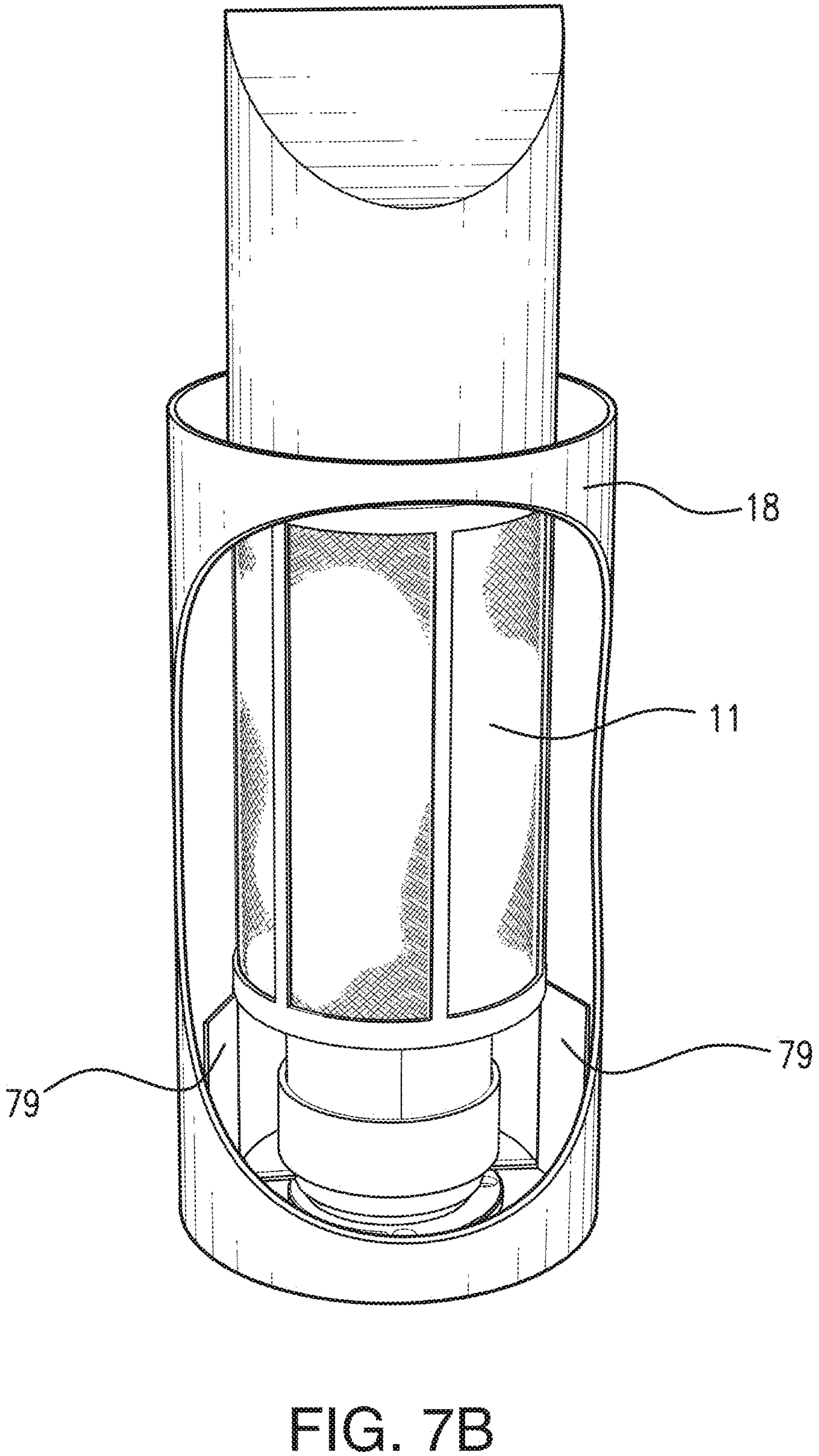

An example embodiment of a device for producing AOPs that is appropriate for mounting in a duct is shown in FIG. 7B. This device comprises a wick structure tube 11 encased by a housing 18. In this embodiment, the wick structure may be molded into a pleated or nodular form, or may comprise hydrophilic granules contained within a screen. The housing comprises a large opening, allowing the outer surfaces of the wick structure 11 to contact air passing through the duct in which it is mounted. A UV lamp or other light source is positioned at the center axis of the wick structure tube (not shown), the length of the light source being the same as the length of the corresponding wick structure. In this embodiment, air is ducted into the inner wick tube, and pushed along the entire wick structure length until finally exiting the wick structure. During this process, the air becomes fully treated, while also carrying the AOP reaction products. Motive force for this transported and treated air is provided either via external capture fins 79 positioned externally to capture and direct forced duct air into the wick structure, or via purpose utilized external fan(s) for non HVAC duct applications. As the air travels through the wick structure and the AORC, it is continually exposed to at least one of light energy, sonolysis reactions, bi-polar ionized forces, and AOP reactants from the in-situ photocatalytic surfaces positioned within the wall of the wick structure.

Figure 7C:
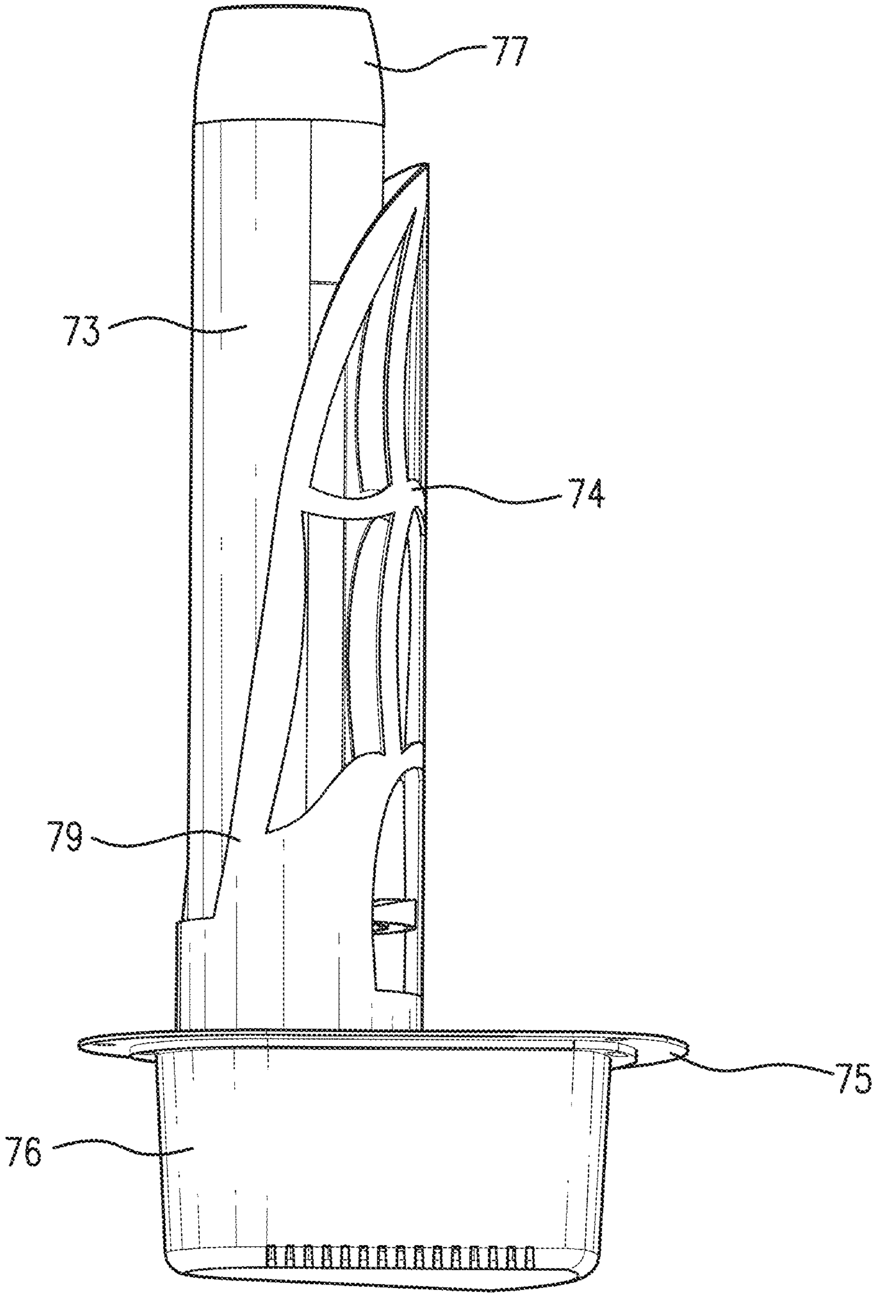

An alternative embodiment of a device for producing AOPs that is appropriate for mounting in a duct is shown in FIG. 7C. In this embodiment, at least a wick structure, a light source, ultrasonic emitters, and digital reflectors are mounted within a protective housing 73. The housing is provided with a cover 74 that comprises a plurality of slots to facilitate air flow to the wick structure. The housing is coupled to a mounting plate 75 which facilitates mounting of the device into a hole within the duct. The device further comprises an additional protective unit 76, which is coupled to the housing and the mounting plate. This protective unit 76 contains the electronic components necessary to operate the light source, the ultrasonic emitters, the heaters, the fan and/or the ion sources contained within the housing. The protective unit 76 is designed to protrude from the outer surfaces of the duct in which the device is mounted.

Figure 7D:
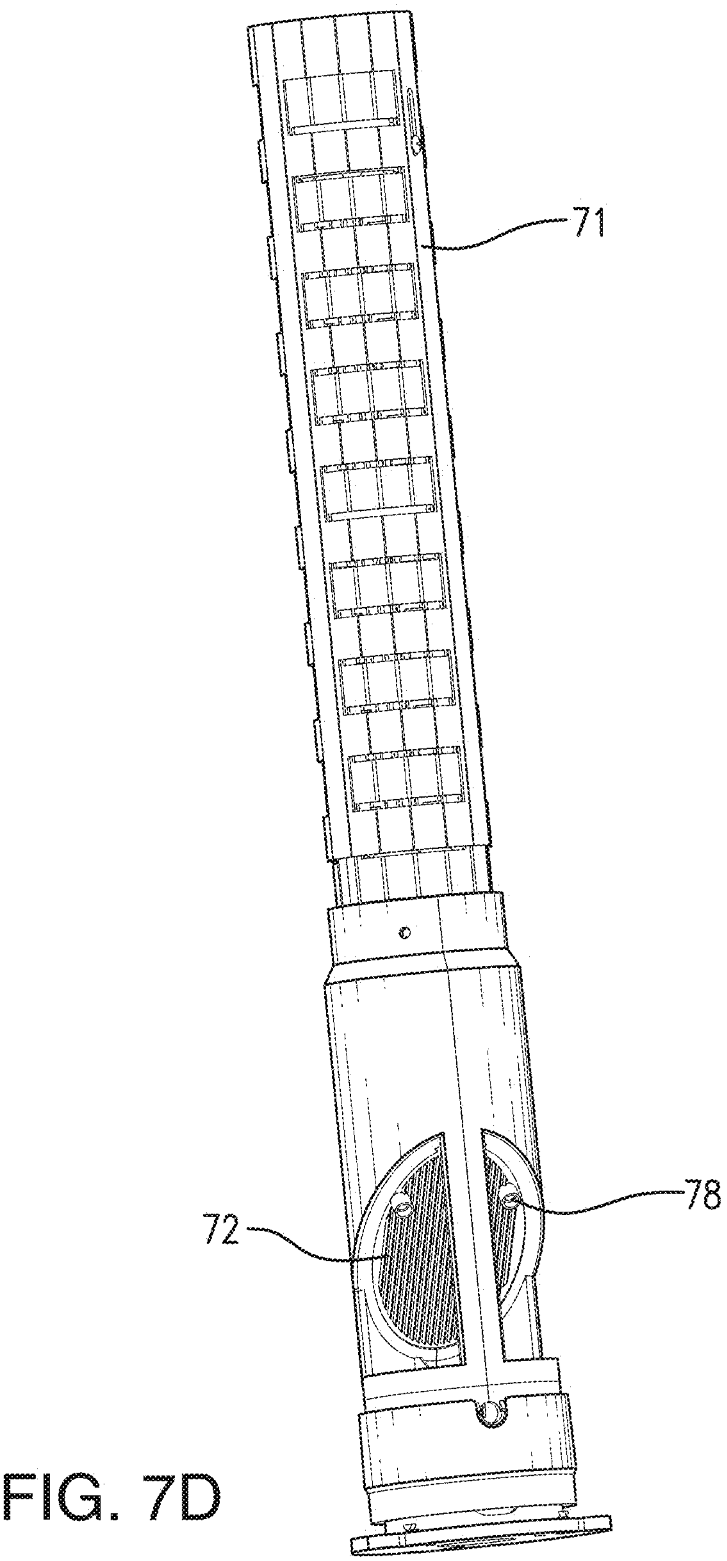
FIG. 7D shows a modular unit which may be incorporated into various devices in accordance with the instant invention.

To facilitate ease of assembly and repair, one or more components of the devices of the instant invention may be manufactured as modular units. In FIG. 7D, a unit comprising a light source, ultrasonic emitters, digital reflectors, and ion emitting electrodes is shown. This unit is referred to herein as the AORC cell. The various components of the AORC cell are contained within a housing 71, which includes an air inlet 72. In this specific embodiment, carbon fibers are attached to the housing 71 via connectors 78, and act as ion producing electrodes at the inner surfaces of the unit. This unit is provided with a quick release feature, which will allow complete replacement of the AORC cell without the use of any tools. This feature allows replacement of the cell by simply twisting the cell, and pulling it out for removal. This facilitates ease of maintenance.

Figure 8A:
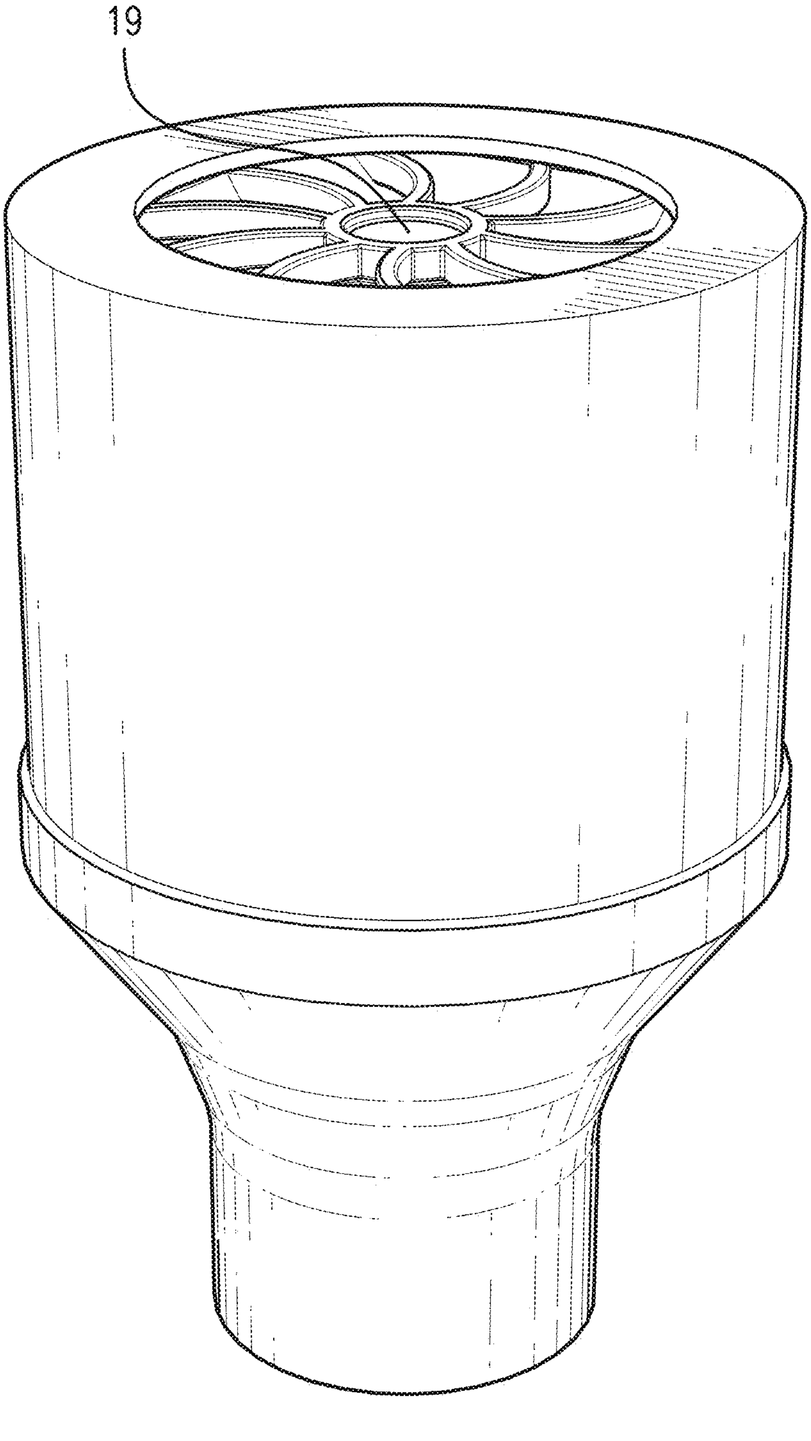
FIGS. 8A and 8B illustrate an alternative embodiment of an apparatus for generating advanced oxidation products, wherein the wick is provided as a cone shaped structure.
Figure 8B:
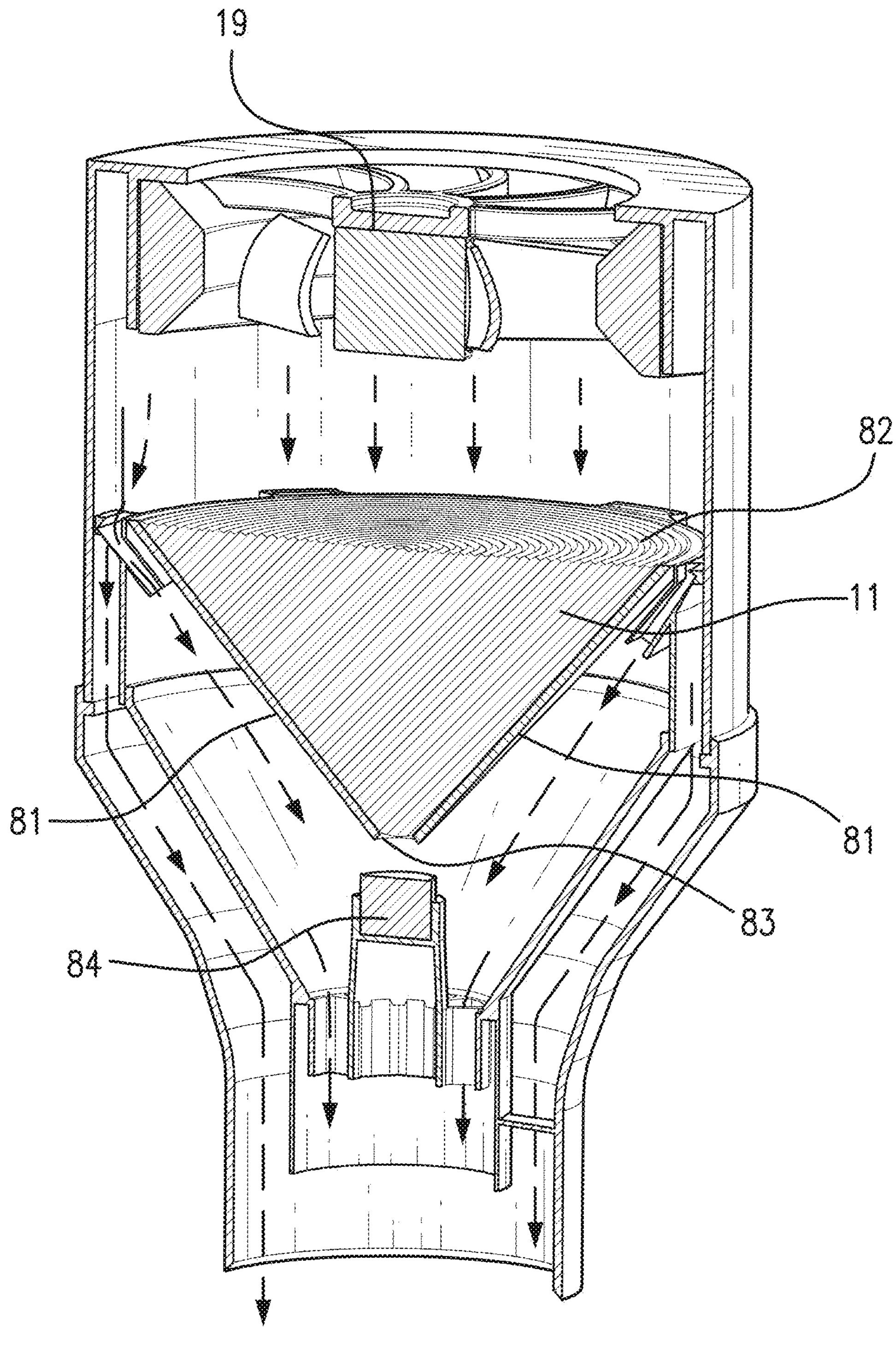

An additional alternative embodiment of the devices for producing AOPs of the instant invention is shown in FIGS. 8A and 8B. In this embodiment, the wick structure 11 is cast into an air sealed conical shaped surface (sealed on the sides of the cone 81). The wick structure is so cast to promote a much higher surface area on the outer surface, increasing the water harvesting area by multiples of 10. In this embodiment, a fan 19 is configured to direct air comprising water vapor towards the top surface 82 of the wick cone. The water collected at the top surface of the cone is funneled and channeled downward towards the tip 83 of the wick cone. The downward movement of the water is directed by gravity and also by vapor pressure differentials.

At the tip of the cone 83, the water exits the wick structure but stays in liquid form until exiting onto a sonic anvil 84 where it is then immediately hit with a narrow directed beam of high amplitude ultrasonic energy. The water is instantaneously vaporized by sonolysis cavitation, creating advanced oxidation reactions via the water itself, without the addition of a photo catalyst reactor or UV source.

Air flow in this embodiment of the device is shown by arrows. Air travels vertically downward from the cone apex, transporting the vaporized water components that recently went through the sonolysis reactions back through the sonic beam. This air mass, moving from the cone apex 83 towards the ultrasonic transducer 84, creates a countercurrent plasma of air that is continually bombarded with ultrasonic energy, promoting the formation of AOPs until the air passes out of the sonic path and moves around and past the transducer. Here the sonolysis induced AOP reactants will continue to react with and also oxidize unwanted chemical compounds in the moving air mass. The countercurrent flow provides increased residence time for the reactions to take place and treatment to occur. Notably, because the same ambient air vapor is collected, and then re-released, there is no net effect on the overall humidity of the ambient environment, while still providing an effective air cleaning device.

The embodiment of FIGS. 8A and 8B may be configured as a stand-alone unit, or may alternatively be configured for mounting in a duct.

In an alternative embodiment, the apparatus may also be used to target and repel nuisance rodents and insects. In this embodiment, ultrasonic energy can be reflected and directed to external surfaces, with the specific intention of targeting the external environment of the ambient spaces containing the wick structure. More specifically, the inner duct space that the wick structure and the AORC are located in is targeted. This is made possible by modifying the digital reflector and a portion of its target points within the wick structure. As shown in FIG. 1A, specific sound channels or slits can be provided in wall openings 16, 17, and in the wick structure wall, so that a portion of the reflected sonic energy can travel from the digital reflectors, pass through the wick structure wall and into the air space external to the wick structure and the AORC.

The specific reflectors located on the main digital reflector array are angled and positioned to facilitate these sound waves exiting the wall. Releasing ultrasonic energy into these ambient duct spaces induces uncomfortable environmental conditions to household pests, including rodents and even susceptible insects. This simple modification in effect causes the AORC and wick structure system to also become a sonic pest deterrent system (as well as an advanced oxidation reactor). In one embodiment of this design the ultrasonic transducers can be configured to emit additional frequencies in the 24 through 60 kHz range. Ideally, varying these emitted frequencies and their amplitude throughout a randomly generated pattern. Doing this will cause the most discomfort to the nuisance pests, as this prevents environmental conditioning to a predictive sonic environment. The pests are prevented from becoming accustomed to either a single steady frequency or a simple patterned generation cycle of multiple frequencies at a constant amplitude.

According to particular embodiments, the devices diagrammed in FIGS. 1A, 7A, 7B, and 7C are configured to generate advanced oxidation products by a process as detailed in the flow chart of FIG. 5.

Method of Forming the Wick Structure

Figure 6:
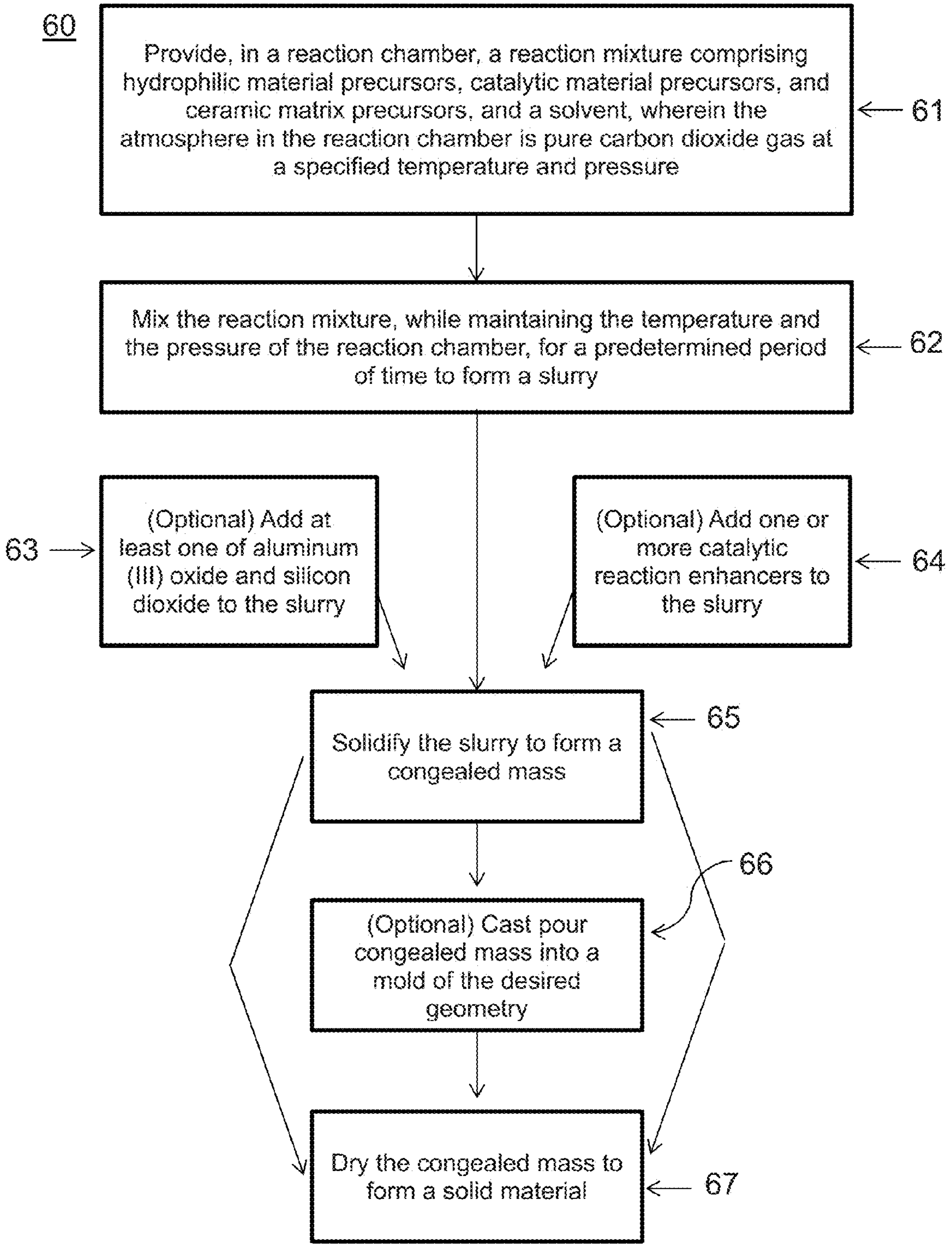
FIG. 6 is a flowchart illustrating a method for producing a wick structure in accordance with exemplary embodiments of the present invention.

Referring now to FIG. 6, a flow chart 60 illustrating a method for producing a wick structure is shown. Briefly, the wick structure is formed by combing precursor materials and mixing to form a slurry, transforming the slurry into a congealed mass, and drying the congealed mass to produce a final solid structure.

The wick structure may be formed from the following precursor materials: magnesium oxide (MgO), titanium tetraisopropoxide (TTIP, $Ti\{OCH(CH_3)_2\}_4$), cerium oxide ($CeO_2$), and aluminum oxide ($Al_2O_3$). Catalytic enhancers including rhodium, silver, copper, zinc, platinum, nickel, erbium, yttrium, fluorine, sodium, ytterbium, boron, nitrogen, phosphorus, oxygen, thulium, silicon, niobium, sulfur, chromium, cobalt, vanadium, iron, manganese, tungsten, ruthenium, gold, palladium, cadmium, and bismuth, and combinations thereof may also be included with the precursor materials for increased catalytic effect of the final structure.

In the first step of the process 61, the precursors, optionally including one or more catalytic enhancers, are combined with a solvent to form a reaction mixture. In one embodiment, the precursors are added to the reaction mixture in this ratio: 27 parts TTIP:74 parts MgO:4 parts cerium oxide:up to 1 part $Al_2O_3$. It is noted that the relative abundance of $MgCO_3$ and $TiO_2$ in the final wick structure matrix can be controlled by adjusting the initial mix ratio of the precursor materials. Changing the ratio of $MgCO_3$ and $TiO_2$ in the final wick structure will change the water absorbance vs. photo reactivity ratio in the final wick structure. The inventors of the instant application have found that a 3:1 ratio of $MgCO_3$ to $TiO_2$ in the final structure is optimal.

The solvent used in the reaction mixture is preferably methanol, but ethanol and inorganic acid additions can also be used in conjunction with the methanol. Variations in the amounts of solvent and acid components may yield longer solution times, thereby affecting the final porosity of the wick structure. It is noted that the higher the rate of porosity in the final wick structure, the more effective the hydraulic attraction (higher water absorption), and the more surface area available for the photocatalytic reactions to occur. The inventors have found that a higher porosity is achieved by increasing the dissolution rate of the $CO_2$ gas into the solvent. In the reaction mixture provided above, 48 parts of methanol would be provided with the 27 parts TTIP:74 parts MgO:4 parts cerium oxide:up to 1 part $Al_2O_3$.

One method of controlling the dissolution of $CO_2$ gas into the solvent in the reaction process is by controlling atmospheric pressure of the reaction chamber. As the reactor vessel pressure increases, the solubility of the methanol increases (Henry's law). At atmospheric pressure methanol already has five times the $CO_2$ solubility as compared to water's $CO_2$ solubility. Secondarily, this process can be aided further by altering the inherent solubility of the methanol itself. Prior to adding the methanol to the reactor, to increase its solubility further, it can actually be chemically altered with a small addition of aluminum oxide ($Al_2O_3$). A 0.05% by weight addition of aluminum oxide will dramatically increase the methanol's solubility to $CO_2$ (doing this additional step will actually increase the methanol's $CO_2$ solubility by nearly 10%). Alternatively, $SiO_2$ may be added at the same rate. However, $Al_2O_3$ is preferred, as addition of this material results in a higher porosity (as well as also requiring less external energy, due to the lower gas pressures for the equivalent solubility). The use of $Al_2O_3$ also has the benefit of aiding in increasing the wick structure's inherent wall strength.

The reaction mixture is provided in a modified gas atmosphere (MGA) reaction chamber. The reaction chamber comprises an internal mixing mechanism to facilitate the continual mixing of components during the reaction process. Mixing may be achieved using devices known to those skilled in the art, such as a paddle blade mixer. The mixing is preferably performed at a speed not exceeding 450 RPM, in order to reduce wall splattering and to ensure optimal mixing of all constituents throughout the reaction. The reaction chamber must also have a suitable means of detecting and displaying both pressure and temperature, as well as gas addition ports, flushing ports, a secondary process component addition port (pressure isolated), and a viewing port. A high pressure relief valve is also recommended.

After the reaction mixture is placed in the reaction chamber, oxygen is purged from the chamber using $CO_2$ gas, to provide a reaction atmosphere of pure $CO_2$ gas. Mixing is then initiated, in step 62. The internal pressure of the reactor is raised to a minimum pressure of 45 PSI, while the reactants are simultaneously heated to a temperature of 140° F. (60° C.). Pressure release steps are often required to maintain a maximum pressure of 45 PSI, until the final reaction temperature is reached and stabilized. The reaction pressure, temperature and mixing is maintained for a minimum of four hours, and results in the formation of a flowing slurry. During the reaction time, the MgO is transformed to $MgCO_3$, and the titanium tetraisopropoxide is simultaneously transformed into anatase titanium dioxide ($TiO_2$). The $MgCO_3$ and the $TiO_2$ comprise a reacted matrix within the slurry with cerium oxide dispersed throughout (with small amount of $Al_2O_3$, added in methanol step and at precursor mixing)

In step 63, after the reaction phase is completed, up to an additional 3.75 parts aluminum (III) oxide is optionally added to and fully mixed into the slurry. This step of adding aluminum (III) oxide specifically after the reactions producing magnesium carbonate and titanium dioxide have occurred and while the base material is still in a flowing slurry results in a more rigid final wick structure. The addition of aluminum (III) oxide at this stage in the process is advantageous when the final wick structure matrix is designated for mold casting because the addition of aluminum (III) oxide at this stage of production yields a material which is mold stable and releasable. In embodiments wherein the final wick structure will not be shaped via mold casting, the step of adding aluminum (III) oxide can be omitted, further increasing final porosity per gram of the wick base material.

Additionally and independently, in step 64, one or more secondary photocatalytic reaction enhancers, selected from rhodium, silver, copper, zinc, platinum, nickel, erbium, yttrium, fluorine, sodium, ytterbium, boron, nitrogen, phosphorus, oxygen, thulium, silicon, niobium, sulfur, chromium, cobalt, vanadium, iron, manganese, tungsten, ruthenium, gold, palladium, cadmium, and bismuth, and combinations thereof can be added to the slurry during this stage of production, if desired. These enhancers should be added through the material additives port.

After the optional addition of aluminum (III) oxide, $SiO_2$, and/or secondary catalytic enhancers, the process heat is discontinued, and the $CO_2$ reactant pressure is raised to 200 PSI. The slurry is mixed for an additional 10 minutes, further increasing the amount of dissolved $CO_2$ in the slurry. After the additional 10 minutes, the mixing is discontinued and the chamber is depressurized through a series of stepped pressure releases. Specifically, the pressure is reduced in increments of 10 PSI at intervals which range from 5 minutes to 2 hours, until the pressure of the chamber is reduced to a final pressure of 15 PSI. The optimal length of the pressure reduction intervals varies depending on the final mix proportions of the reaction mixture. This pressure is then maintained for the remainder of this phase of production, referred to herein as the congealing phase.

In step 65, the congealing phase, the initial conversion of the slurry to a solid phase begins. This stage of production may take up to 5 days, and is halted at first indications of solidification. During this time, the reaction chamber is kept closed and no mixing is performed. Further, the pure $CO_2$ atmosphere of the vessel is maintained, and the pressure is kept at a stable 15 PSI. As long as ambient temperatures are maintained at approximately 70 to 80° F. (21 to 27° C.), no external heat is applied.

The pressure reduction steps described above produce successive micro off gassing events (effervescence) of the $CO_2$ gas into the wick structure slurry base material during the congealing phase. This stepped effervescence event increases the internal surface area of the solidifying matrix. If the solidifying process is delayed, a re-pressurization step and repeat of this stepped process is performed.

Once the material begins to congeal it can then be cast poured into molds of desired geometries, if desired, according to step 66. Ideally this step is also performed under a 15 PSI $CO_2$ atmosphere.

Once the slurry has solidified, the chamber is finally fully depressurized and brought to ambient air conditions. It is then removed from the reactor vessel, either present in molds or in granular form.

The next step 67 is the drying phase, which comprises two stages. The preliminary drying phase is referred to herein as the low temperature drying process. In this process, the material that is either cast within the molds (the high $Al_2O_3$ product), or in unmolded granular form (with the very low $Al_2O_3$) and is heated to 160° F. (71° C.) for 36 hours. This step drives off any remaining solvent and further hardens the entire mass.

In exemplary embodiments, the material may additionally be soaked in deionized water (Millipore prepared) to completely hydrolyze any remaining titanium IV into anatase titanium dioxide. However, performance of this additional step will increase preparation costs due to longer drying times required to slowly expunge excess water, and will also result in diminished pore sizes in the internal structures prior to calcination.

After the initial low temperature drying process, a final calcination step (high temperature drying step) is performed to fully activate the components of the wick structure. The calcination step serves several important functions. First, this step removes any remaining inorganic material from the internal wick structures (crevices and pores) thereby greatly increasing the final porosity and water absorbance of the material (up to 50% greater surface area). This step is also essential to fully activate the formed $TiO_2$, ensuring anatase crystallization, and to prepare the surface of the $TiO_2$ crystals for eventual photo activation. This calcination step further binds the cerium oxide ($CeO_2$), and aluminum oxide ($Al_2O_3$) into a hard ceramic matrix, greatly increasing the overall strength of the wick structure.

The calcination step is performed by slowly increasing the temperature of the wick structure from ambient temperature to 650° F. (343° C.) over the course of 8 hours. It is essential that the initial temperature ramp up to 650° F. be performed very slowly. Proceeding too quickly at this step will cause the materials to expand too rapidly (especially if there is any fluid, i.e. water left over from the Titania IV hydration reaction additions, etc.) and will cause physical damage to the materials and the pore structures (i.e. micro steam induced explosions cause by trapped water in the tiny pores not yet fully opened by the calcination process). Thus, it is highly desirable to level off the ramp temperature increase and hold the temperature at 180° F. (82° C.) for 3 hours before continuing with the original cure ramp rate. Once the temperature is at 650° F. (343° C.), the temperature is maintained for 12 hours to fully activate the system components. A higher calcination temperature may be used to help reduce process time. However, the temperature should never exceed 1000° F. (538° C.) at any time during this process. At temperatures above 1000° F. (538° C.), the anatase crystals will be converted into less desirable rutile crystals. Also, a 60 minute hold time is the minimum required to achieve the desired calcination effect to the $MgCO_3$ in the wick structure.

The inventors of the instant application have performed the calcination process in a kiln fired at 20% excess oxygen, and alternatively with material being purged in a kiln with a 100% nitrogen atmosphere. Activation occurred in both tests, and produced the desired properties in the final wick structure. However, it was found that the 20% excess oxygen environment provided a better overall result for the desired hybrid performance (hydration enhancement and catalyst activation).

Once the calcination step completed, temperatures are ramped down at 100° F. (38° C.) per hour until ambient temperature is reached. After the wick structure has cooled, the dried material is removed either as fully activated granules, or is released/removed from the molds as ready to use wick structure.

SUMMARY

The advanced oxidation processes, as provided by alternative embodiments of the present invention in view of the discussion above, consist of reactions with any combination of hydroxyl radicals, super oxide ions, hydro peroxides, ozonide ions, and hydroxides, and other such advanced oxidation products, that revert back to oxygen and hydrogen after the oxidation of the pollutants. Additionally, in certain alternative embodiments, germicidal UV light rays can additionally help destroy microorganisms, such as germs, molds, viruses, and bacteria. In this way, the advanced oxidation processes, and optionally in combination with any germicidal U.V. light rays, clean and purify an environment by reducing microorganisms, odors, and other undesirable chemicals in the environment. The advanced oxidation processes, as provided by the alternative embodiments of the present invention, can be very useful in many different applications, as should be obvious to those of ordinary skill in the art in view of the discussion above.

While there has been illustrated and described what are presently considered to be the preferred embodiments of the present invention, it will be understood by those of ordinary skill in the art that various other modifications may be made, and equivalents may be substituted, without departing from the true scope of the present invention. Additionally, many modifications may be made to adapt a particular situation to the teachings of the present invention without departing from the central inventive concept described herein. Furthermore, an embodiment of the present invention may not include all of the features described above. Therefore, it is intended that the present invention not be limited to the particular embodiments disclosed, but that the invention include all embodiments falling within the scope of the appended claims.

What is claimed is:

1. A wick structure comprising a base material, wherein the base material is porous and comprises a hydrophilic material, a catalytic material, and a ceramic matrix, wherein the catalytic material comprises titanium dioxide, wherein at least a portion of the titanium dioxide is in anatase crystal form, and wherein the hydrophilic material comprises magnesium carbonate and is formulated to absorb and release water.

2. The wick structure of claim 1, wherein the ceramic matrix comprises cerium oxide and aluminum oxide.

3. The wick structure of claim 1, wherein greater than 99% of the titanium dioxide is in anatase crystal form.

4. The wick structure of claim 1, wherein the base material further comprises one or more additional catalytic materials.

5. The wick structure of claim 4, wherein the one or more additional catalytic materials are selected from the group consisting of rhodium, silver, copper, zinc, platinum, nickel, erbium, yttrium, fluorine, sodium, ytterbium, boron, nitrogen, phosphorus, oxygen, thulium, silicon, niobium, sulfur, chromium, cobalt, vanadium, iron, manganese, tungsten, ruthenium, gold, palladium, cadmium, and bismuth, and combinations thereof.

6. The wick structure of claim 2, wherein the cerium oxide and the aluminum oxide form a ceramic matrix that provides structural support.

7. The wick structure of claim 1, wherein the magnesium carbonate forms a sponge-like structure that is infused with the titanium dioxide.

8. The wick structure of claim 1, wherein the magnesium carbonate is anhydrous and amorphic.

9. The wick structure of claim 1, wherein the base material comprises channels and pores, and has an internal surface area of at least 750 $m^2$ per gram.

10. The wick structure of claim 1, wherein at least a portion of the titanium dioxide is in the form of nanoparticles.

11. The wick structure of claim 1, wherein the wick structure is a longitudinal tube having an exterior surface and an interior surface.

12. The wick structure of claim 11, wherein a surface area of the exterior surface of the longitudinal tube is at least 50% greater than a surface area of the interior surface.

13. The wick structure of claim 11, wherein at least one of the interior surface and the exterior surface comprises v-shaped pleats.

14. The wick structure of claim 11, wherein at least one of the interior surface and the exterior surface comprises convex nodules.

15. The wick structure of claim 1, wherein the wick structure is a conical shaped structure.

16. The wick structure of claim 11, wherein at least one of the interior surface and the exterior surface comprises a screen.

* * * * *